US010960172B2

(12) United States Patent
Merrell et al.

(10) Patent No.: US 10,960,172 B2
(45) Date of Patent: Mar. 30, 2021

(54) BAG AND VALVE FOR ADVANCED RESPIRATORY SUPPORT

(71) Applicant: Compact Medical Solutions LLC, Indianapolis, IN (US)

(72) Inventors: Jonathan Merrell, Indianapolis, IN (US); Anthony Parker, Wilkinson, IN (US); Matthew Haws, Noblesville, IN (US); Adam Scott, Anderson, IN (US)

(73) Assignee: COMPACT MEDICAL SOLUTIONS, LLC, Indianapolis, IN (US)

( * ) Notice: Subject to any disclaimer, the term of this patent is extended or adjusted under 35 U.S.C. 154(b) by 0 days.

(21) Appl. No.: 16/687,269

(22) Filed: Nov. 18, 2019

(65) Prior Publication Data

US 2020/0345967 A1 Nov. 5, 2020

Related U.S. Application Data

(60) Provisional application No. 62/843,140, filed on May 3, 2019.

(51) Int. Cl.
*A61M 16/20* (2006.01)
*A61M 16/00* (2006.01)

(52) U.S. Cl.
CPC ........ *A61M 16/201* (2014.02); *A61M 16/006* (2014.02); *A61M 16/0078* (2013.01); *A61M 16/209* (2014.02)

(58) Field of Classification Search
CPC ............ A61M 16/201; A61M 16/0078; A61M 16/209; A61M 16/006; A61M 16/0084; A61M 16/0081
See application file for complete search history.

(56) References Cited

U.S. PATENT DOCUMENTS

| 4,898,166 A | 2/1990 | Rose et al. |
| 5,109,840 A * | 5/1992 | Daleiden ............. A61M 16/208 |
| | | 128/205.13 |

(Continued)

FOREIGN PATENT DOCUMENTS

| CN | 108654014 A | 10/2018 |
| CN | 208287315 U | 12/2018 |

(Continued)

OTHER PUBLICATIONS

International Search Report and Written Opinion for PCT Application No. PCT/US2019/062005, dated Feb. 28, 2020.

*Primary Examiner* — Margaret M Luarca
(74) *Attorney, Agent, or Firm* — Merchant & Gould P.C.

(57) ABSTRACT

A respiratory device for providing respiratory support to a patient. The device includes an expandable bag portion and a connection member in fluid communication with the expandable bag portion. The expandable bag portion includes an air intake valve and has an adjustable predetermined tidal volume. The connection member includes a positive end expiratory pressure (PEEP) valve, a PEEP controller configured to control the pressure of the PEEP valve, a two-way valve configured to allow air to move from the expandable bag portion in a first direction and through the PEEP valve in an opposing direction, a pressure relief valve configured to vent excess pressure from the connection member to an external environment, and a patient breathing interface.

24 Claims, 20 Drawing Sheets

(56) References Cited

U.S. PATENT DOCUMENTS

| | | | | |
|---|---|---|---|---|
| 5,301,667 | A * | 4/1994 | McGrail | A61M 16/208 128/205.13 |
| 5,558,371 | A | 9/1996 | Lordo | |
| 5,787,880 | A | 8/1998 | Swanson et al. | |
| 7,172,557 | B1 * | 2/2007 | Parker | A61B 5/087 128/200.24 |
| 8,936,024 | B2 * | 1/2015 | Pearce | A61M 16/0084 128/205.14 |
| 9,861,775 | B1 * | 1/2018 | Farmer | A61M 16/06 |
| 2002/0029779 | A1 * | 3/2002 | Schmidt | A61M 15/0086 128/205.25 |
| 2002/0117173 | A1 * | 8/2002 | Lynn | A61M 16/105 128/202.28 |
| 2006/0266358 | A1 * | 11/2006 | Hoogland | A61M 16/0084 128/205.13 |
| 2010/0236557 | A1 | 9/2010 | Reisman | |
| 2014/0107518 | A1 | 4/2014 | Korneff | |
| 2014/0318544 | A1 * | 10/2014 | Murphy | A61M 16/0078 128/205.14 |
| 2016/0256661 | A1 * | 9/2016 | Battersby | A61M 16/0078 |
| 2017/0157348 | A1 | 6/2017 | Gillespie et al. | |
| 2019/0366029 | A1 * | 12/2019 | Prabhudesai | A61M 16/20 |

FOREIGN PATENT DOCUMENTS

| | | | | |
|---|---|---|---|---|
| EP | 0421007 A1 * | 4/1991 | | A61M 16/0084 |
| WO | 2018035137 A1 | 2/2018 | | |

* cited by examiner

BAG AND VALVE FOR ADVANCED RESPIRATORY SUPPORT

PRIORITY CLAIM

This application claims priority to U.S. Provisional Application Ser. No. 62/843,140, filed on May 3, 2019, the entire disclosure of which is hereby expressly incorporated herein by reference.

TECHNICAL FIELD

The present disclosure relates generally to a bag-valve-mask or resuscitator used to ventilate patients in a field setting.

BACKGROUND

A manual resuscitator, or a bag-valve-mask (BVM), is a device used to temporarily push air into the lungs of a patient who is unconscious or otherwise unable to breathe on their own. These devices are found in hospitals and in ambulances throughout the country and in most developed parts of the world.

BVMs have existed for many years. Numerous modifications and enhancements have been made to BVMs over the years, these include enhanced 2-way valves, the addition of a high-pressure relieving "pop-off" valve, and the attachment of an oxygen reservoir to the bag to increase the percent of oxygen content of air flowing into the self-inflating bag portion of the device.

Self-inflating or self-expanding bags are bulky. They typically hold over a liter of air (in an adult model) even when not in use. Two-way valves are also bulky, and make use of a rigid plastic construct that is most commonly shaped in a 90-degree angle. The mask is similarly bulky and typically employs a rigid plastic triangular-shaped device with a soft rubber balloon about a perimeter that interfaces with and forms a seal around the mouth and nose of a victim. Each of these components is bulky in its own right and together, these form a device that is too large and obtuse to be carried in public by individuals who are trained to use them. Thus, when an emergency arises in most non-clinical settings, a BVM is not typically available until after an ambulance has arrived.

Efforts have been made in the past to reduce the overall space occupied by these devices. This includes an entirely collapsible bag with a flexible hollow body that can be stowed into a container. In attempts to make the device smaller, thinner materials have been used. This results in bag-valve-masks that are suitable for one-time use, due to the device losing functionality after its use. Therefore, BVMs are typically only available in a hospital setting or similar clinical location.

In addition to their bulk, traditional BVMs are prone to cause hyperventilation. A condition in which a patient is given too much air. This can result in death. Traditional BVMs cause hyperventilation because they inflate too rapidly, leading lifesavers to give breaths more frequently than is recommended.

Finally, traditional BVMs are only capable of delivering a fixed tidal volume depending on the size of the BVM (adult, pediatric, or neonatal).

SUMMARY

In general terms, this disclosure is directed towards a respiratory device having an expandable bag and a connection member. The respiratory device allows a user to provide respiratory support to a patient.

In an example embodiment, a respiratory device is described. The respiratory device includes an expandable bag and a connection member. The expandable bag includes an air intake valve, the expandable bag has an adjustable predetermined tidal volume. The connection member is in fluid communication with the expandable bag portion and includes the following elements: a positive end expiratory pressure (PEEP) valve, a PEEP controller configured to control the pressure of the PEEP valve, a two-way valve configured to allow air to move from the expandable bag portion in a first direction and through the PEEP valve in an opposing direction, a pressure relief valve configured to vent excess pressure from the connection member to an external environment, and a patient breathing interface.

In a further aspect, a method of providing respiratory support to a patient is described. The method includes providing a respiratory device including an expandable bag and a connection member. A predetermined tidal volume of the expandable bag is selected. A pressure of a PEEP valve is selected with a PEEP controller. The user is able to compress the expandable bag to provide air to the patient.

Corresponding reference characters indicate corresponding parts throughout the several views. The exemplifications set out herein illustrate an embodiment of the invention, and such exemplifications are not to be construed as limiting the scope of the invention in any manner.

BRIEF DESCRIPTION OF THE DRAWINGS

The inventive aspects of the present disclosure can be more easily understood, and further advantages and uses thereof can be more readily apparent, when considered in view of the detailed description and the following figures in which.

DETAILED DESCRIPTION

Figure 1:
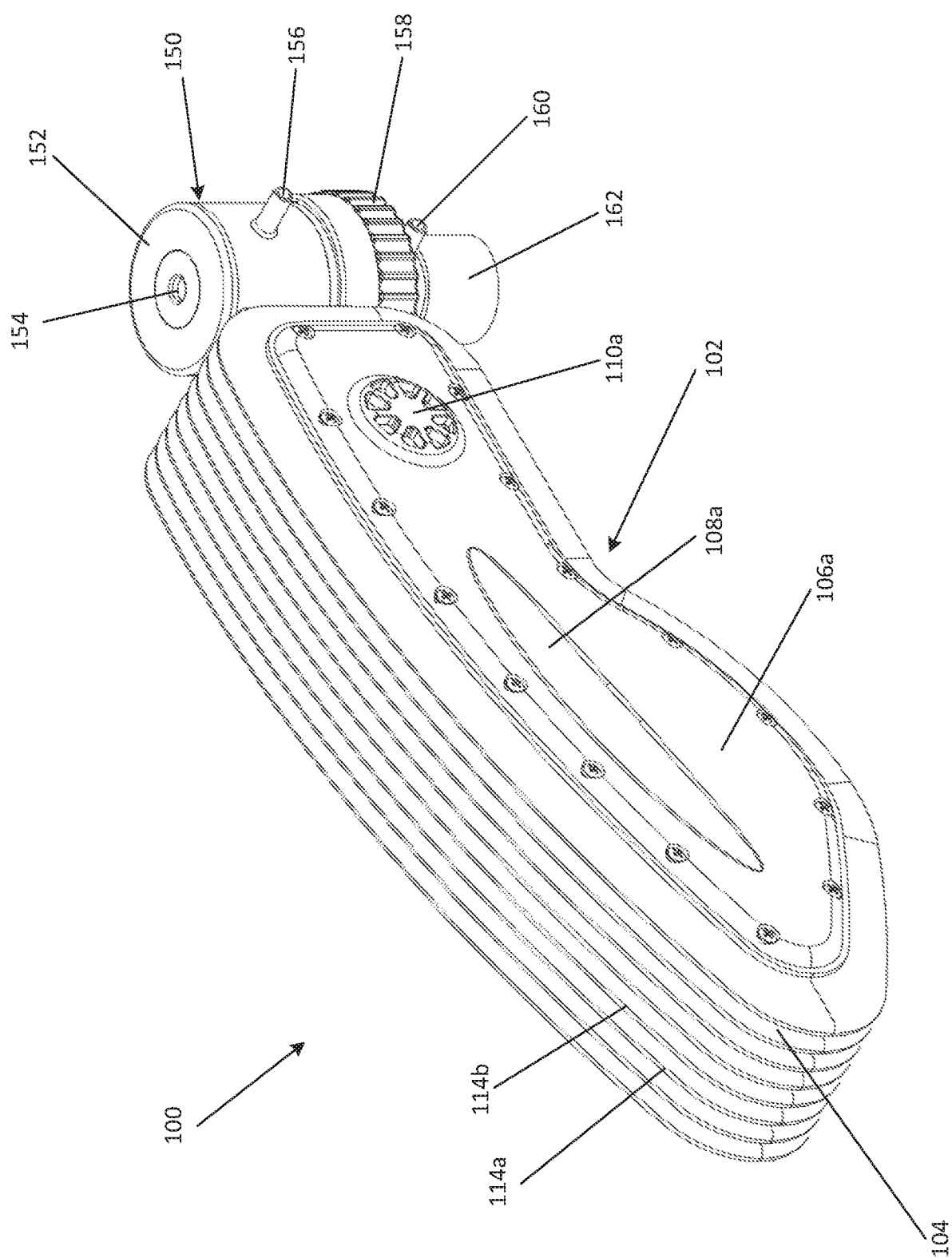
FIG. 1 illustrates an example embodiment of an expandable bag having features that are examples of inventive aspects in accordance with the present disclosure.

The figures and descriptions provided herein may have been simplified to illustrate aspects that are relevant for a clear understanding of the herein described devices, systems, and methods, while eliminating, for the purpose of clarity, other aspects that may be found in typical devices, systems, and methods. Those of ordinary skill may recognize that other elements and/or operations may be desirable and/or necessary to implement the devices, systems, and methods described herein. Because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Generally, bag-valve-masks (BVM) are comprised of three key components: a self-inflating bag, a two-way valve, and a mask. The bag is designed to expand, fill and retain a volume of air. This volume constitutes the next "breath" that a patient is to receive. When the bag is compressed by a lifesaver's hand (herein referred to as the user), the breath is pushed through a valve and down into the mask portion of the device. The mask is kept in contact with the patient's face and directs the breath downward and into the mouth or nasal passage of the patient and into their lungs. When the bag compression is released, the bag expands and a new volume of "fresh" air is drawn into the bag while the original breath of "used" air exits the patient and is released into the ambient air via the two-way valve.

The disclosure is directed generally to a BVM device having an expandable bag and a connection member is fluid communication with the expandable bag. More specifically, the respiratory device is able to provide different tidal volumes and different PEEP values to a patient.

FIG. 1 illustrates an example embodiment of an expandable bag device 100. The expandable bag device 100 includes an expandable bag portion 102 and connection member 150. The expandable bag device 100 may be attached to any type and size of mask or other patient breathing interface device, such as an endotracheal tube or laryngeal mask airway. The expandable bag portion 102 includes an expandable bag 104, a first side portion 106a, second side portion (not shown), a first handle portion 108a, a second handle portion (not shown), and at least one air intake valve 110.

In an example embodiment, the expandable bag 104 has an accordion-like design, comprising a plurality of folds 114a, 114b, such as a bellow, or other similar mechanism. The plurality of folds 114 allows the expandable bag 104 to expand and contract. This allows the expandable bag 104 to occupy minimal space when not in use. The expandable bag 104 can be made from a variety of materials such as flexible plastics. The expandable bag 104 includes a side portion 106 that is stiffer than the expandable bag 104 to allow a user to hold the side portion 106a to compress the expandable bag 104. The side portion 106a is made from a plastic that has a rigidity greater than the expandable bag 104. The side portion 106a also comprises a handle portion 108a. The handle portion 108a may optionally be raised or depressed from the side portion 106a to provide a surface for a user's fingers to grip and/or grab when compressing the expandable bag 104.

The rigidity of the side portion 106a allows a user to press against it in order to compress the expandable bag 104. This allows a user to compress the expandable bag portion 102 fully, as when a user compresses the side portions 106a, the side portion 106a compresses the entire length of the expandable bag 104.

The side portions 106 may also be configured to be easily held in a user's hand. In an example, the side portions 106 may each include an angled plate that makes it easier for the user to hold in one hand while inflating and deflating the bag even if the user's grip is relaxed on the expandable bag 104. Additionally or alternatively, the side portions 106 may include a grip material, such as rubber that makes it easily to hold. In yet another embodiment, the side portions 106 include a recess or legs that a user can grip with their hand. In yet another embodiment the side portions 106 could include a strap (not shown) to help the user maintain contact with the sides of the device.

The side portion 106a and expandable bag 104 also include an air intake valve 110a. The air intake valve 110 extends through the side portion 106a and into the expandable bag 104. The air intake valve 110a provides the expandable bag 104 with ambient air intake to re-inflate the expandable bag 104. Each side portion 106 may comprise an air intake valve 110.

The expandable bag 104 is a self-inflating bag, in which the expandable bag 104 takes on an expanded configuration without any external input from the environment. The interior of the expandable bag 104 includes a spring, which is described in more detail below.

The expandable bag portion 102 is connected to a connection member 150. The connection member 150 includes a pressure relief valve 154 located at the top 152 of the connection member 150, a dial 158, and a mask connection member 162. In an embodiment, the pressure relief valve 154 is a one-way valve that only lets air flow from inside the connection member 150 to the external environment.

The dial 158 controls the positive end expiratory pressure (PEEP) valve, which is the controlled resistance of the exhaled airflow. The dial 158 controls the location of side portions of an internal valve, such as a barrel valve (shown in FIGS. 13-17). When the dial 158 is turned up, the side portions move closer together, so it is harder for the patient to exhale against. The dial 158 can have different values such as from 0 to 20 mmHg. Alternatively, a push button (shown in FIG. 20) may be used to control PEEP.

The connection member 150 also includes two optional external pressure gauge connection members 156, 160. The optional external pressure gauge connection members 156, 160 can be used to indicate the internal pressure levels of different components of the expandable bag device 100. The external pressure gauge connection member 156, 160 can be used to measure the pressure of a patient's lungs upon inspiration (PIP—peak inspiratory pressure). The external pressure gauge connection member 156, 160 can be used to measure the pressure of the patient's lungs during exhalation (PEEP). In other embodiments, these two valves are not present, or are capable of being closed.

Figure 2:
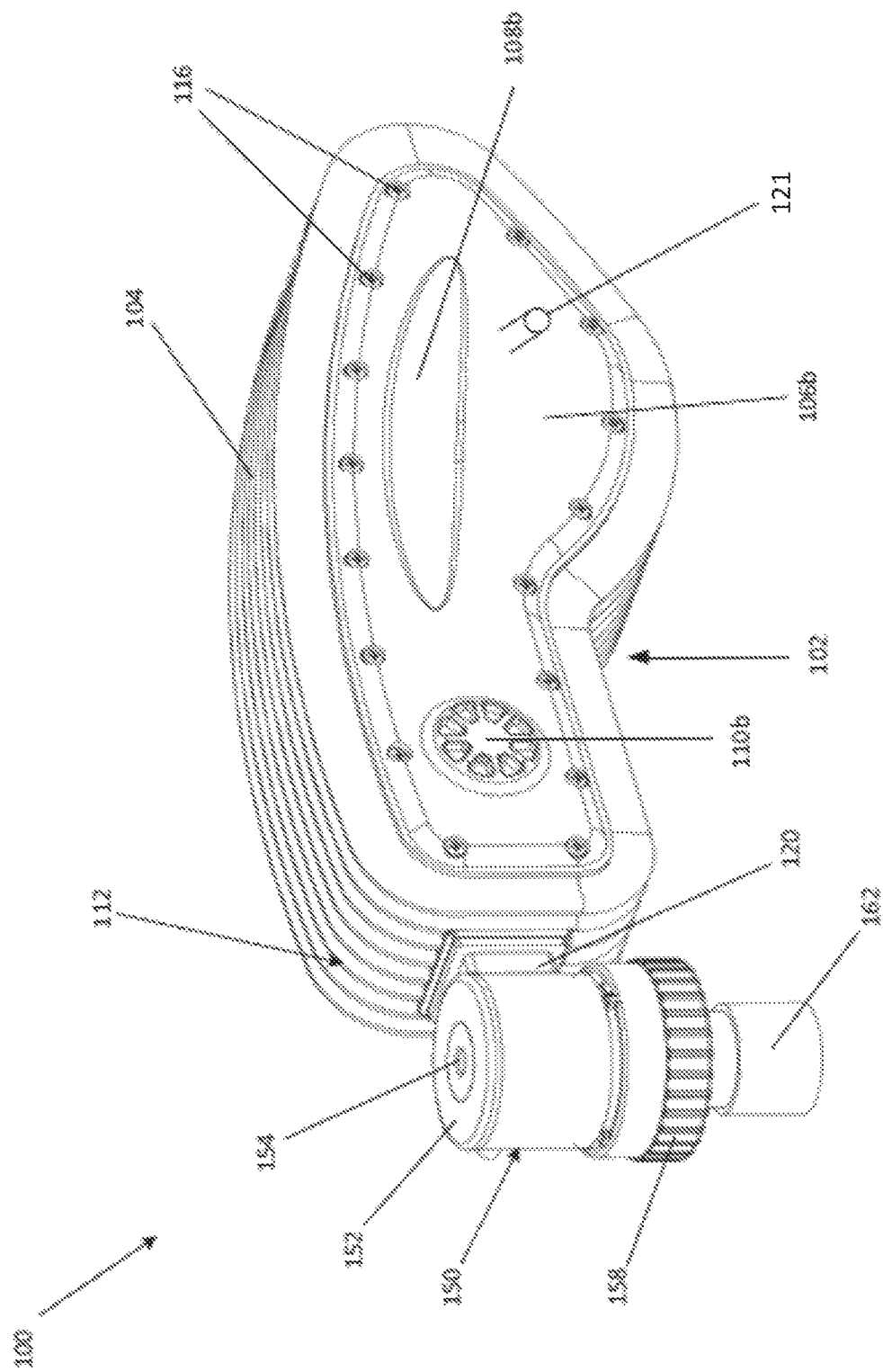
FIG. 2 illustrates a perspective view of the back side of the expandable bag of FIG. 1.

FIG. 2 illustrates a rear view of the expandable bag device 100. As shown, the expandable bag portion 102 includes a second side portion 106b having a handle portion 108b, and a second air intake valve 110b. The second side portion 106b having a handle portion 108b and the second air intake valve 110b are the same as the side portion 106a, handle portion 108a, and air intake valve 110a shown in FIG. 1, and the descriptions of which are omitted for the sake of brevity. The first side portion 106a and the second side portion 106b sandwich the expandable bag 104.

Attachment points 116 are located along each side portion 106 to attach each side portion 106 to the expandable bag 104. Various types of attachment mechanisms may be used to attach each side portion 106 to the expandable bag 104, such as adhesives or mechanical connections.

Still referring to FIG. 2, the expandable bag 104 is attached to the connection member 150 via the valve connection member 120. The connection member 150 may be fixedly connected to the expandable bag portion 102, or alternatively, may be removable. In a removable embodiment, an attachment mechanism may be selected from a snap fit, friction fit, or other similar mechanism.

In an example embodiment, the connection member 150 includes an "over-breathing" valve (not shown). As shown in more detail at FIG. 17, the over-breathing valve allows a patient to breathe on their own, even without the expandable bag 104 providing the air. For example, if a patient has a mask on, and the patient can or begins to breathe on their own, the over-breathing valve allows the patient to breathe.

The expandable bag device 100 is shaped such that it takes up minimal space during storage. When the expandable bag device 100 is not being used, a mask (not shown) is detachable from the connection member 150, and can be stored next to the expandable bag portion 102. In order to take up minimal space, the expandable bag portion 102 has a shape that allows the mask portion to abut against it, such as having the expandable bag portion 102 having a rounded concave shape. Still further, the expandable bag device 100 is designed so the expandable bag portion 102 is compressible and does not hold any air when not in use.

The expandable bag device 100 is configured to be used by a user to provide respiratory support to a patient. In use, the expandable bag device 100 is connected to a mask (not shown), which provides air to a patient in need. The expandable bag device 100 is biasable at the articulation point 112, by a user. The articulation point 112 maintains the expandable bag 104 in an open or expanded configuration (shown in more detail below at FIGS. 11-12). When a user compresses the side portions 106, the expandable bag 104 condenses, which forces air through the valve connection member 120 (discussed in more detail below), through the connection member 150 and into a mask (not shown). Alternatively, the connection member 150 may be connected to a different patient breathing interface, such as an endotracheal tube, an end-tidal $CO_2$ connector, or a laryngeal mask airway.

In an embodiment, the articulation point 112 is a spring located within the expandable bag 104. The articulation point 112 may be made from a material such as metal, fiberglass, carbon fiber, plastic, or any other structural material that will bias the expandable bag 104 in an inflated or expanded configuration. The articulation point 112 has a strength great enough to keep the bag open when not subject to external forces, but weak enough that a user can squeeze the side portions 106, which bias the articulation point 112 with one hand. Still further, the articulation point 112 is designed with a material that does not allow the expandable bag 104 to open too quickly. For example, the articulation point 112 comprises a hinge that is configured to inflate the expandable bag 104 in 5-6 seconds; however, other time periods may be utilized.

The expandable bag device 100 is configured such that when a user compresses the side portions 106, the entire expandable bag 104 is compressed. This allows the expandable bag 104 to have a size that is the volume of air needed, without having to be oversized. This also allows the expandable bag 104 to be as compact as possible.

When a user desires to provide subsequent "breaths," the user relaxes the compression on the side portions 106 of the expandable bag 104, which allows the expandable bag 104 to expand into the expanded configuration. The air intake valves 110 allows air to move from an external environment to the inside of the expandable bag 104.

In another embodiment, the expandable bag portion 102 further comprises a valve connection member 120 which can be connected to a source of oxygen (not shown). In use, the oxygen source will instill a predetermined volume of pure oxygen in the expandable bag portion 102. When the expandable bag portion 102 is expanded, it would pull in ambient air from the periphery to blend with the oxygen from the oxygen source which is coupled to the expandable bag 102 by the connector.

The tubing connector 121 may further include an indicator (not shown) that indicates to the user that oxygen is flowing into the expandable bag 104. An example indicator may be a flap, a spinner, or a valve that moves due to the flow of oxygen, and the user is able to see the movement of the indicator. In such an example, the indicator may be translucent and the indicator may be colored. In another example, the indicator may have a noise-making device that whistles when oxygen is flowing through the indicator into the expandable bag 104.

Figure 3:
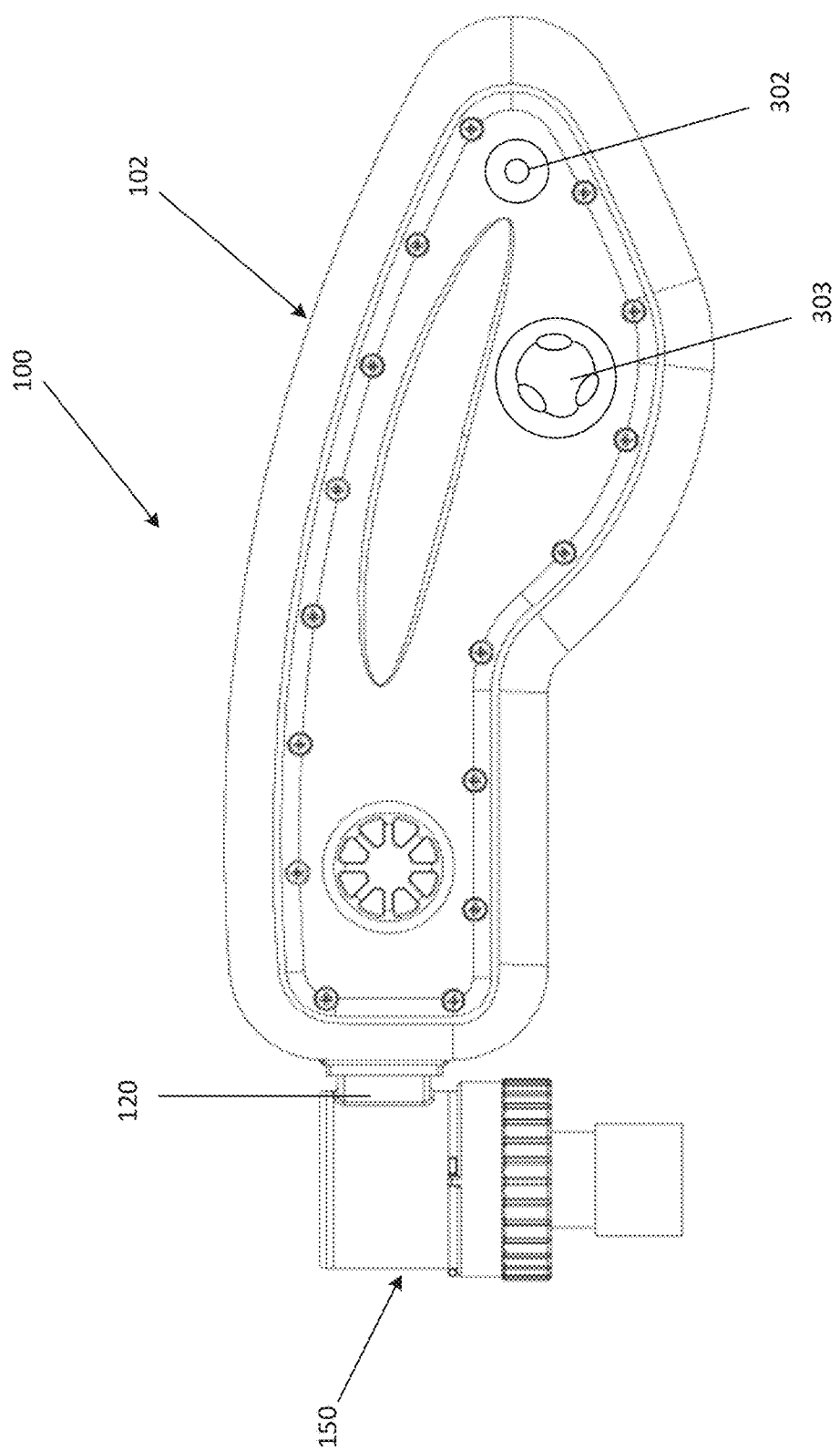
FIG. 3 illustrates a first side view of the expandable bag.

FIG. 3 illustrates a side view of the expandable bag device 100. The valve connection member 120 connects the expandable bag portion 102 to the connection member 150. The valve connection member 120 includes a lumen, and may or may not include a valve. In an embodiment comprising a valve, the valve is a one-way valve that only allows air to move from the expandable bag portion 102 to the connection member 150.

In an example embodiment, the expandable bag portion 102 also includes a strap buckle 302. The strap buckle 302 allows a strap (not shown) to be connected to a first side portion 106a and a second side portion 106b. The length of the strap can determine how much the expandable bag 104 can expand. For example, a strap with a first length connected to each of the strap buckles 302 restricts the expandable bag 104 from opening more than a first predetermined fill volume. A strap with a second length can restrict the expandable bag 104 from opening more than a second predetermined fill volume. This allows the expandable bag device 100 to be used on patients with different sizes of lungs. For example, a short strap may be required for a neonatal patient and a long strap for a pediatric patient. No strap may be required for an adult patient.

In an alternative embodiment, a single strap may include multiple buckles at predetermined lengths, so a single strap may be used for different predetermined fill volumes. The strap can include indicia that indicates which buckle is to be used with each type of patient.

The straps (not shown) may include indicia on each that conveys pertinent information for the resuscitation of each patient size. For example, the shorter strap for older pediatric patients might remind a user to give 15 compressions for 2 rescue breaths when cardiopulmonary resuscitation is given by the user.

In yet another embodiment, a dial or push button mechanism 303 may be used to control the tidal volume. The push button mechanism 303 controls how large the expandable bag 102 is able to expand. For example, the push button mechanism 303 may include 3 different pre-determined volumes, such as a tidal volume for a neonatal patient, a second tidal volume for a pediatric patient, and a third tidal volume for an adult patient. This allows the expandable bag device 100 to be used on patients with different sizes of lungs.

Figure 4:
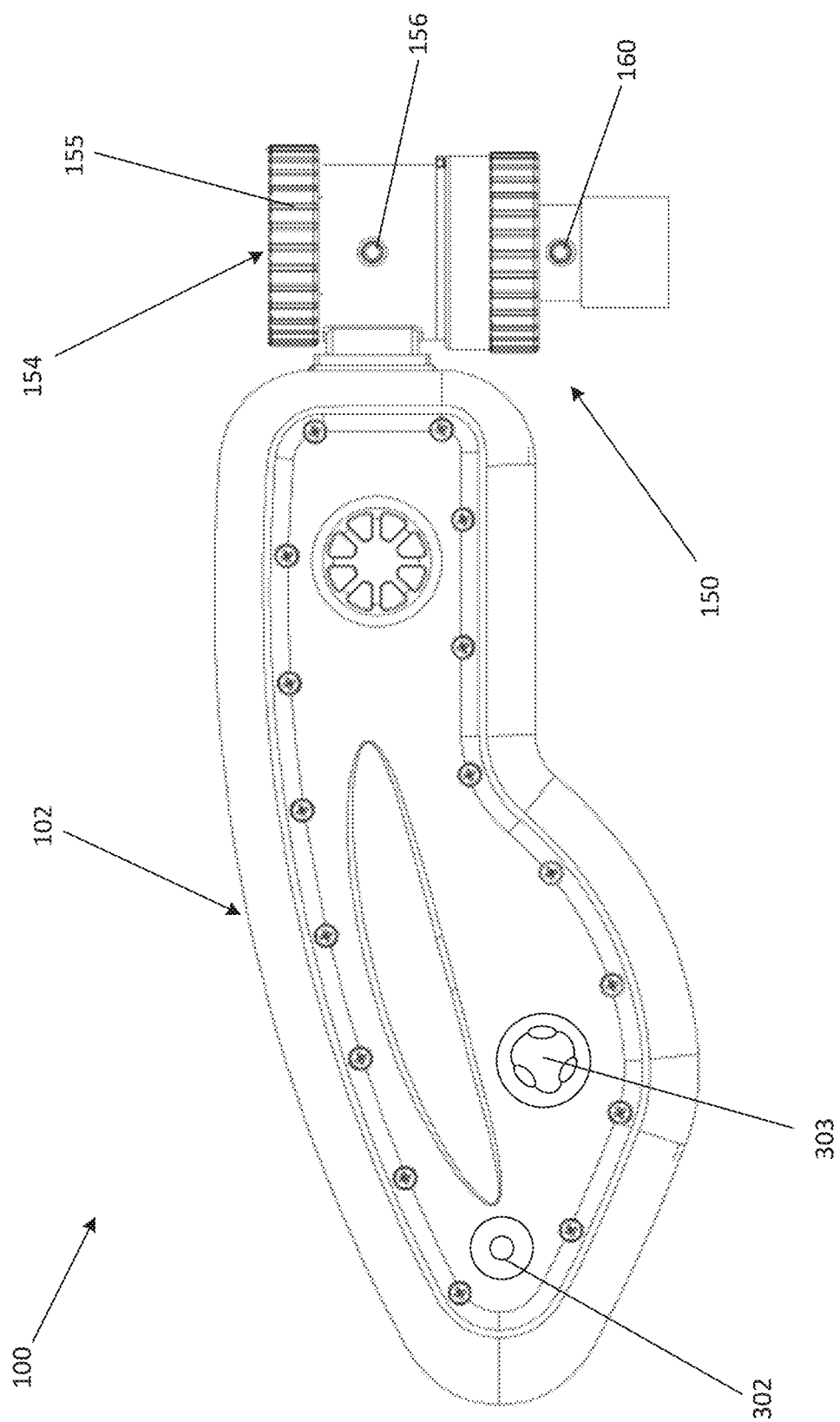
FIG. 4 illustrates a second side view of the expandable bag.

FIG. 4 illustrates an opposing side view of the expandable bag device 100. In an example embodiment, the connection member 150 includes a first external pressure gauge connection member 156 and a second external pressure gauge connection member 160. As described above, these external pressure gauge connection members 156, 160 allow a user to attach a pressure gauge to determine the pressure provided or received at each of the external pressure gauge connection members 156, 160. The opposing side also includes a strap buckle 302, the details of which are omitted for brevity.

In an embodiment, the pressure relief valve 154 includes a dial 155 that allows the pressure at which the pressure relief valve 154 vents air to be adjustable. In an embodiment, the pressure relief valve 154 is configured to vent air at a pressure of 40 cm water. In another embodiment, the pressure at which the pressure relief valve 154 vents air is adjustable. An adjustable pressure relief valve 154 may be controllable the dial 155 or other similar mechanism.

Figure 5:
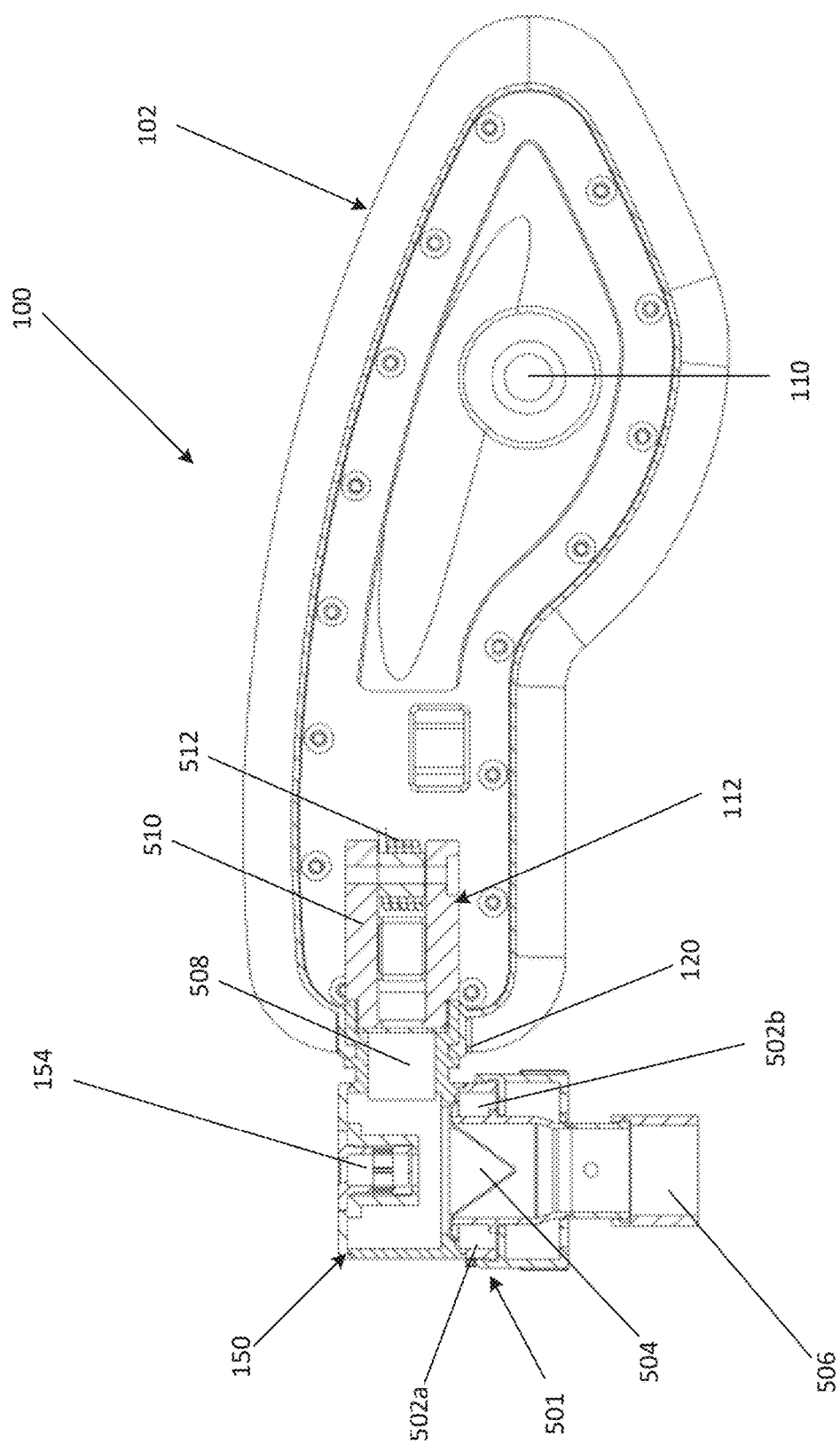
FIG. 5 illustrates a vertical cross-sectional view of the expandable bag of FIG. 1.

FIG. 5 illustrates a vertical cross-sectional view of the expandable bag device 100. The connection member 150 includes the pressure relief valve 154 located at the top of the connection member 150, a PEEP valve 501, and a two-way valve a located above a mask connection lumen 506. The two-way valve 504 may be a duckbilled valve.

The pressure relief valve 154 may be a ball-and-spring valve that relieves excess pressure. Alternatively, the pressure relief valve 154 may be a pop-off valve, a stiffened duck-billed or other type of valve. The pressure relief valve 154 is a one-way valve, so air only moves from the inside of the connection member 150 to the external environment.

The PEEP valve 501 may be comprises of two separate valves, each located lateral to the two-way valve 504. In an example embodiment, the PEEP valve 501 includes two barrel valves 502. For example, a first side of the barrel valve 502a is located on a first side of the two-way valve 504 and a second side of the barrel valve 502b is located on a second side of the two-way valve 504. This is shown in more detail at FIGS. 13-16. As described above, the PEEP valve 501 is controlled by the dial 158.

The two-way valve 504 allows air to move from the connection member 150 through the mask connection lumen 506 into a mask (not shown) for a patient to breathe. This is shown in more detail at FIGS. 13-16.

In an alternative embodiment, the PEEP valve 501 may be a different type of valve, such as a torsion valve or a compression valve. Other types of valves include duckbill, diaphragm, spool, butterfly, needle, ball, gate, poppet, plug, and flapper.

The expandable bag device 100 is biasable at the articulation point 112. The expandable bag portion 102 includes a biasing member 512 connected to front side and back side of the expandable bag 104 at connection point 510. The biasing member 512 may be a spring, or other type of member that allows the bag to articulate at the articulation point 112. The biasing member 512 has a strength such that it does not cause the expandable bag 104 to open too quickly when in use. Other types of biasing members include but are not limited to torsion, compression, extension, bow, leaf, conical, flat, and disk/cup members.

Also shown is the air intake valve 110 of the expandable bag 104. The air intake valve 110 allows air from the external environment to fill the expandable bag 104. The air intake vale 110 may further include an indicator (not shown) that indicates to the user that the expandable bag 104 is inflating and when the expandable bag 104 has completed inflating. An example indicator may have a noise-making device that whistles when the expandable bag 104 is inflating and stops making noise when the expandable bag 104 is full. For example, the indicator may be made from a flexible material, such as a thin plastic or thin rubber.

Figure 6:
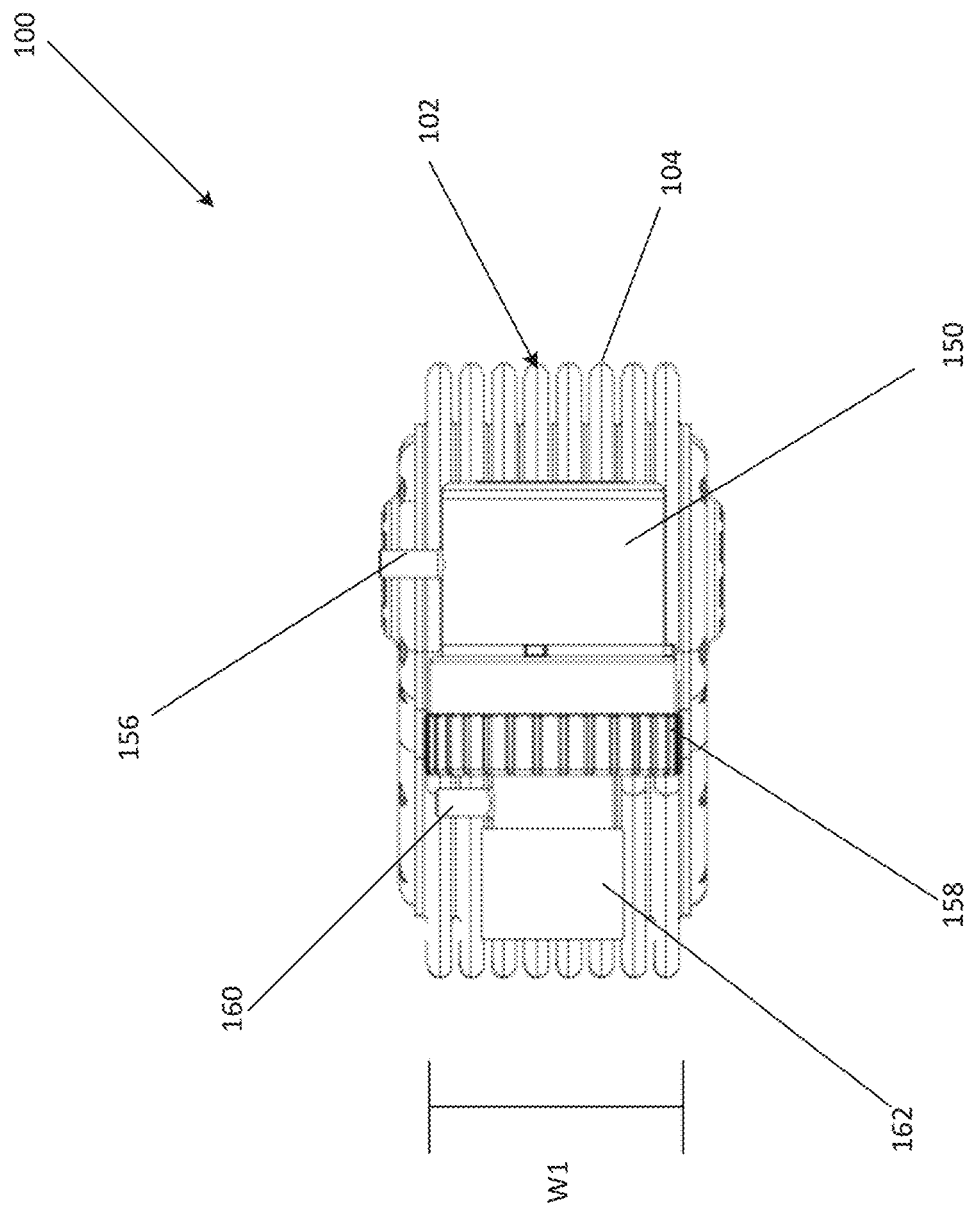
FIG. 6 illustrates a third side view of the expandable bag.

FIG. 6 illustrates a view of the connection member 150 with the expandable bag portion 102 located behind it. As shown, the expandable bag 104 of the expandable bag portion 102 is compressed. In a compressed configuration, the expandable bag 104 has a width of a first end that is the same as a width of an opposing end. For example, the width $w_1$ of the expandable bag portion 102 may be from about 2 cm to about 15 cm.

Figure 7:
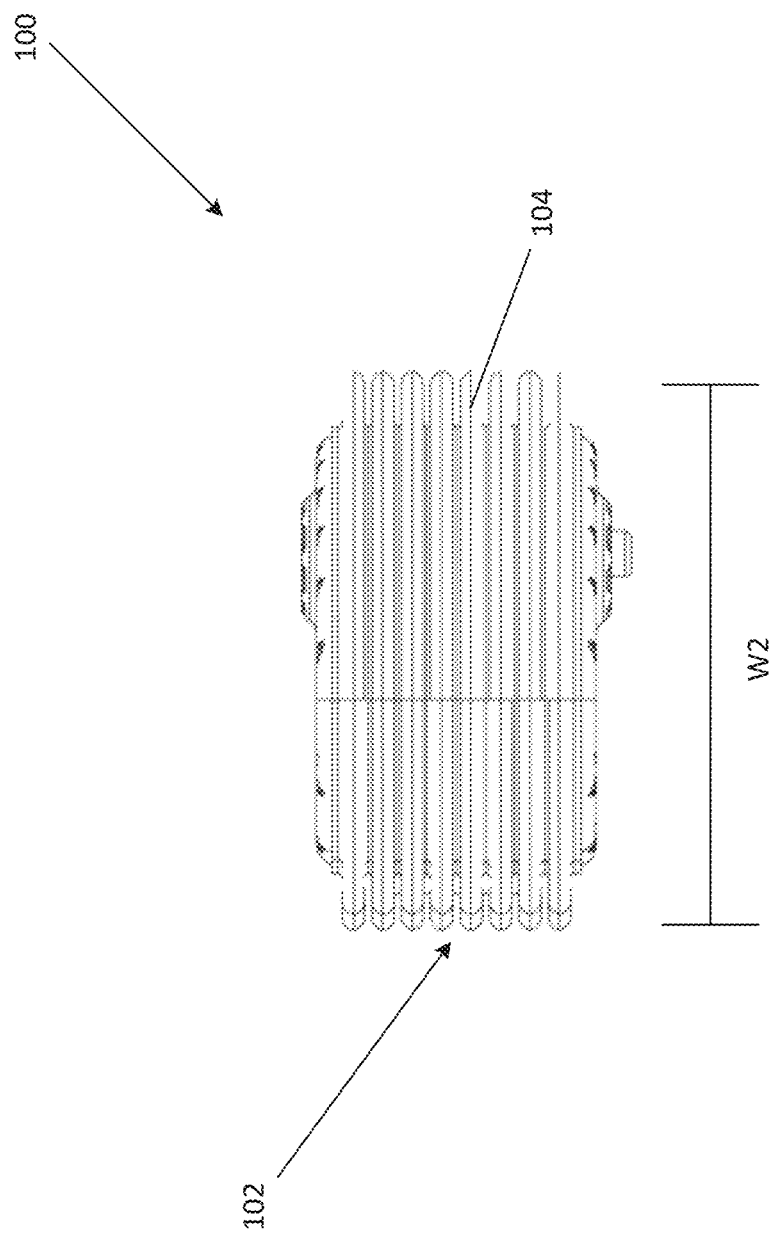
FIG. 7 illustrates a fourth side view of the expandable bag.

FIG. 7 illustrates another view of the expandable bag portion 102 in a compressed configuration. In an embodiment, a second width $w_2$ of the expandable bag portion 102 may be from about 4 cm to about 30 cm.

Figure 8:
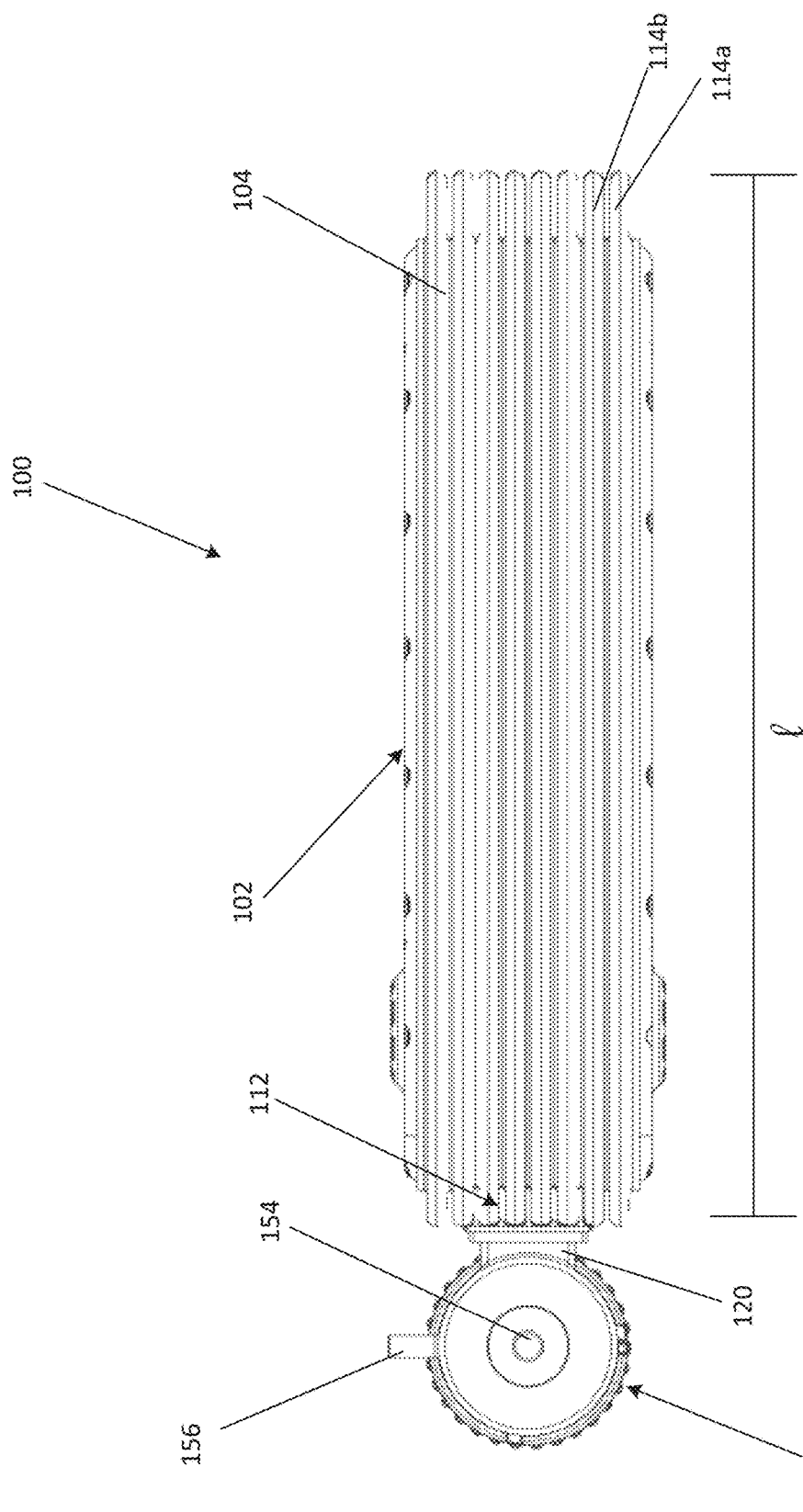
FIG. 8 illustrates a top view of the expandable bag.

FIG. 8 illustrates a top view of the expandable bag device 100. The expandable bag 104 has an accordion-type shape including a plurality of folds 114a, 114b. The plurality of folds 114 enables the expandable bag 104 to expand to a maximum capacity. A maximum capacity may be one fluid liter. In alternative embodiments, the maximum capacity may be more, such as 1.5 fluid leaders, or less, such as 0.5 fluid leaders. The length l of the expandable bag portion 102 may be from about 5 cm to about 50 cm.

The expandable bag 104 includes the articulation point 112 at an end connected to the connection member 150. The opposing end of the expandable bag 104 expands when articulation point 112 is in a biased configuration.

The top portion of the connection member 150 comprises the pressure relief valve 154. As discussed above, the pressure relief valve 154 allows air to flow from the connection member 150 to the external environment in the event that excessive pressures are applied to a patient's lungs.

Figure 9:
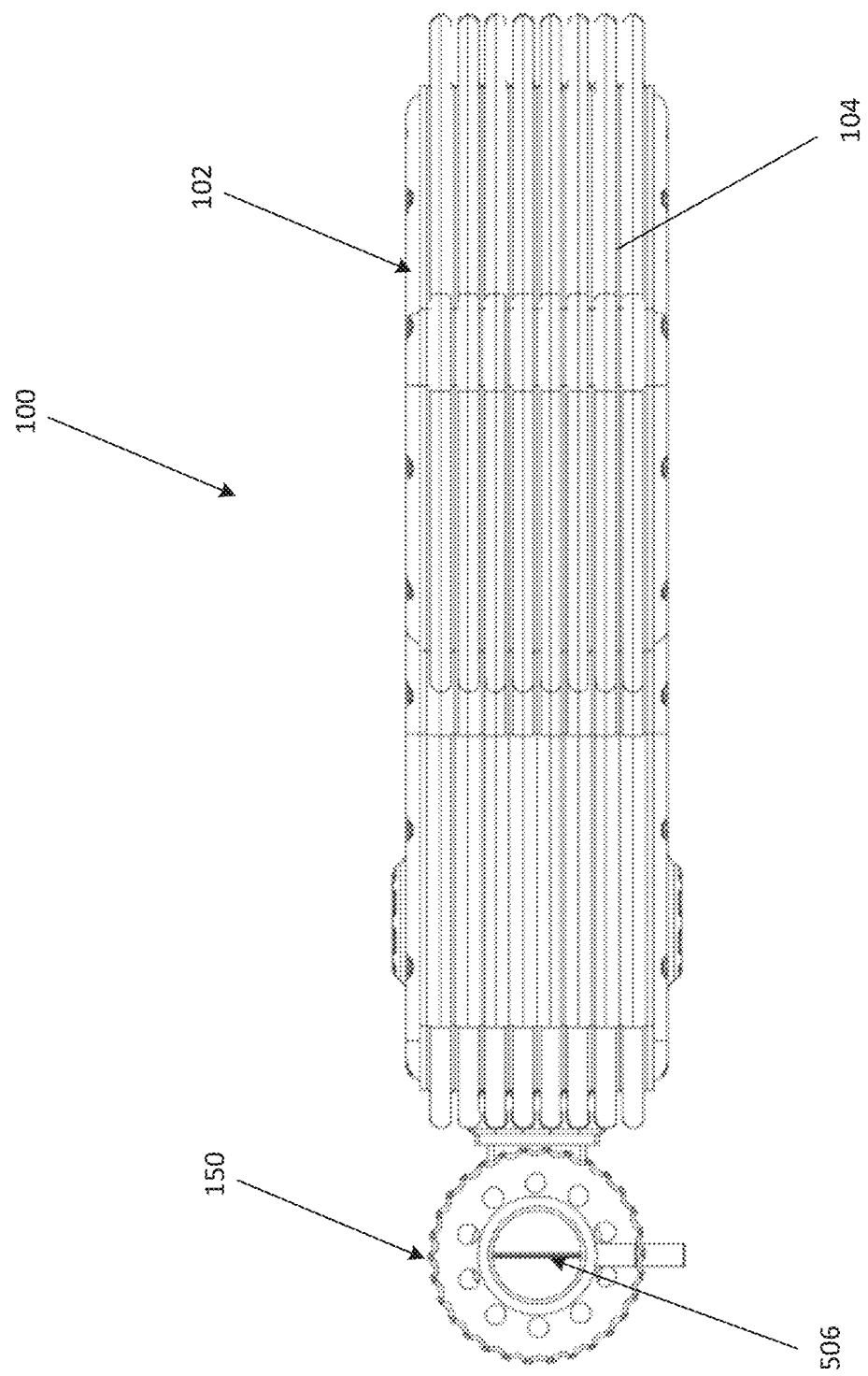
FIG. 9 illustrates a bottom view of the expandable bag.

FIG. 9 illustrates a bottom view of the expandable bag device 100. The connection member 150 includes the mask connection lumen 506, which allows the connection member 150 to connect to a mask or other patient breathing interface unit (not shown).

Figure 10:
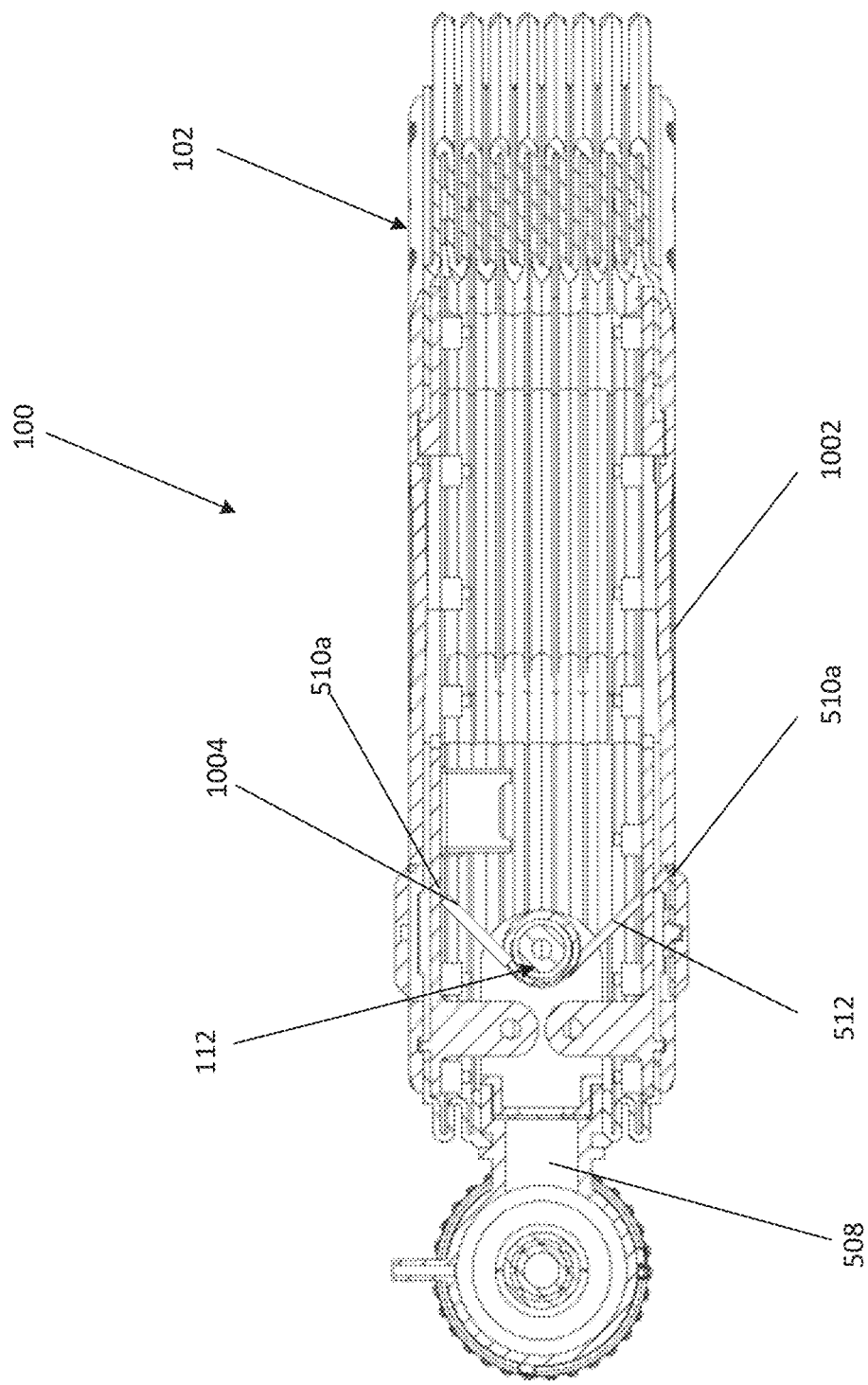
FIG. 10 illustrates a horizontal cross-sectional view of the expandable bag.

FIG. 10 illustrates a horizontal cross-sectional view of the expandable bag device 100. Articulation point 112 is located at a first end of the expandable bag portion 102. The articulation point 112 is configured to maintain an open expanded configuration, until at which time pressure is applied externally to the expandable bag portion 102 to collapse the expandable bag 104 by a user. The biasing member 512 is connected to front side 1002 and back side 1004 of the expandable bag 104 at connection point 510a, 510b. The biasing member 512 may be a spring, or other type of member that allows the bag to articulate at the articulation point 112. Other types of biasing members include but are not limited to torsion, compression, extension, bow, leaf, conical, flat, and disk/cup members.

Figure 11:
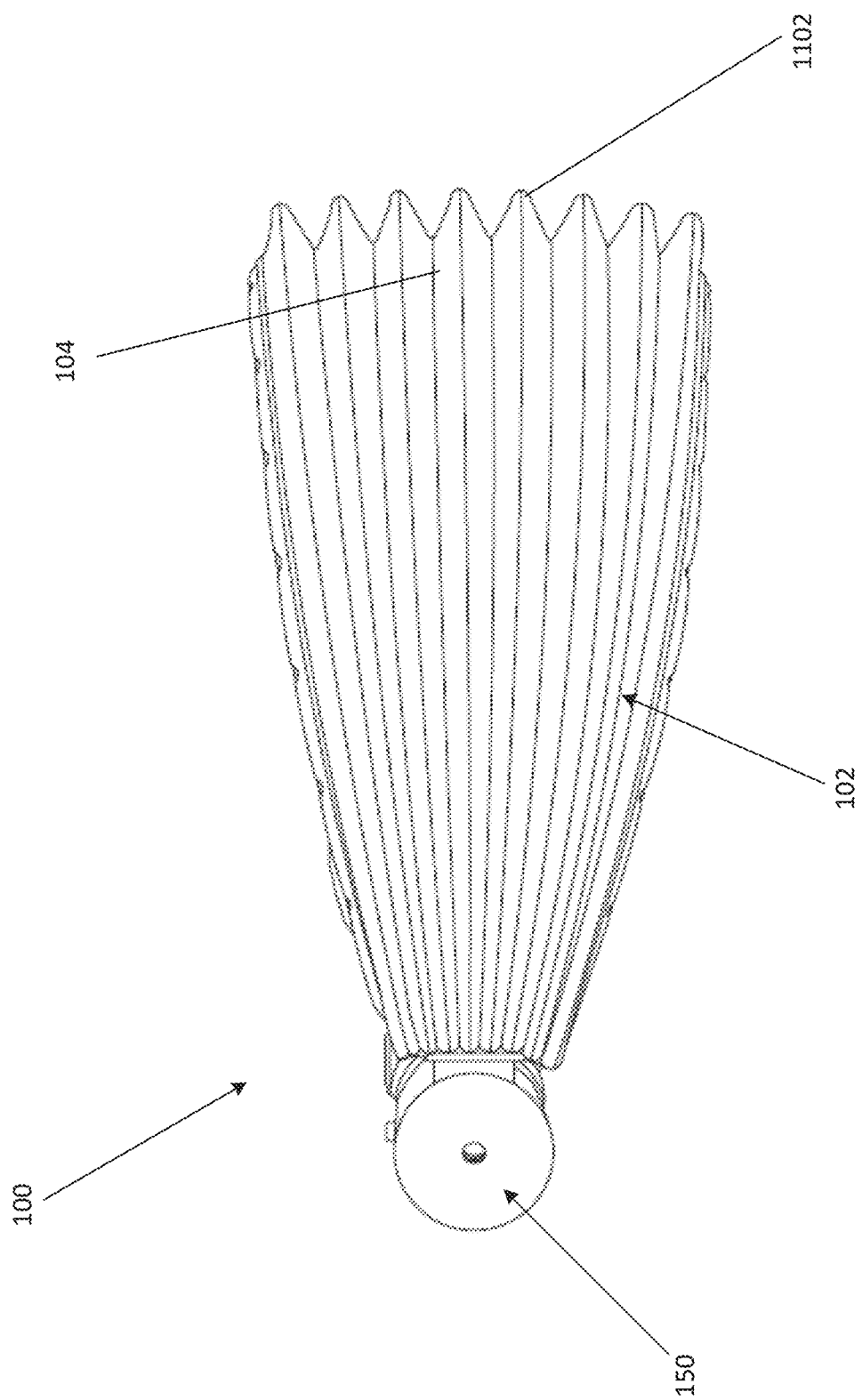
FIG. 11 illustrates a top view of the expandable bag in an expanded configuration.

FIG. 11 illustrates a top view of the expandable bag device 100 in an expanded configuration. As shown, the expandable bag portion 102 has a generally triangular-shape when in an expanded configuration. The bag could assume other shapes such as spherical, ovoid, square, rectangular, or other polygonal shape. The end 1102 of the expandable bag portion 102 opposite the connection member 150 is expanded, allowing the expandable bag 104 to fill with air. The biasing member (not shown) opens the expandable bag to a predetermined fluid volume.

Figure 12:
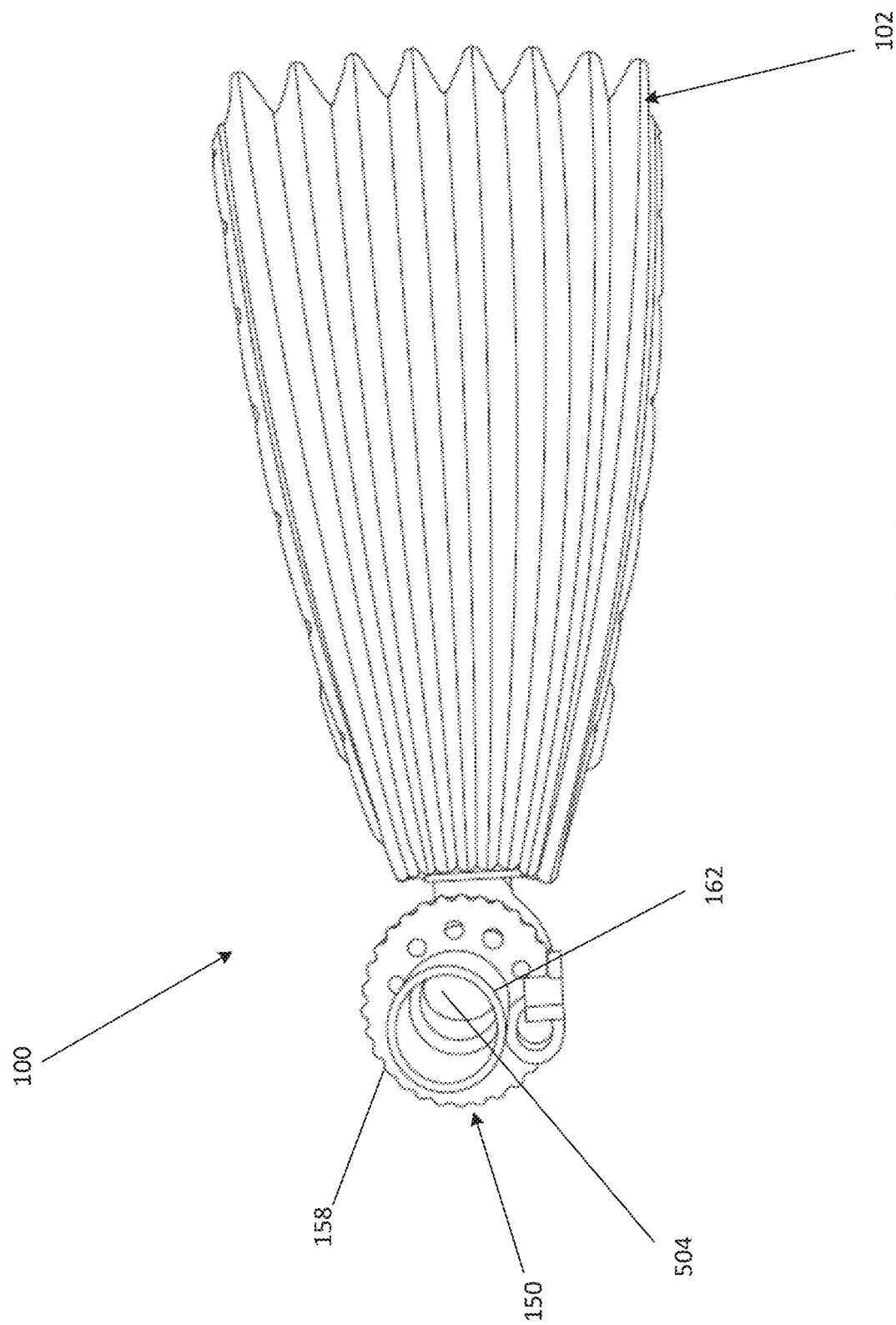
FIG. 12 illustrates a bottom view of the expandable bag in an expanded configuration.

FIG. 12 illustrates the expandable bag device 100 from a bottom viewpoint, in an expanded configuration. The connection member 150 includes a mask connection member 162 and the two-way valve 504 located within the mask connection lumen 506.

Figure 13:
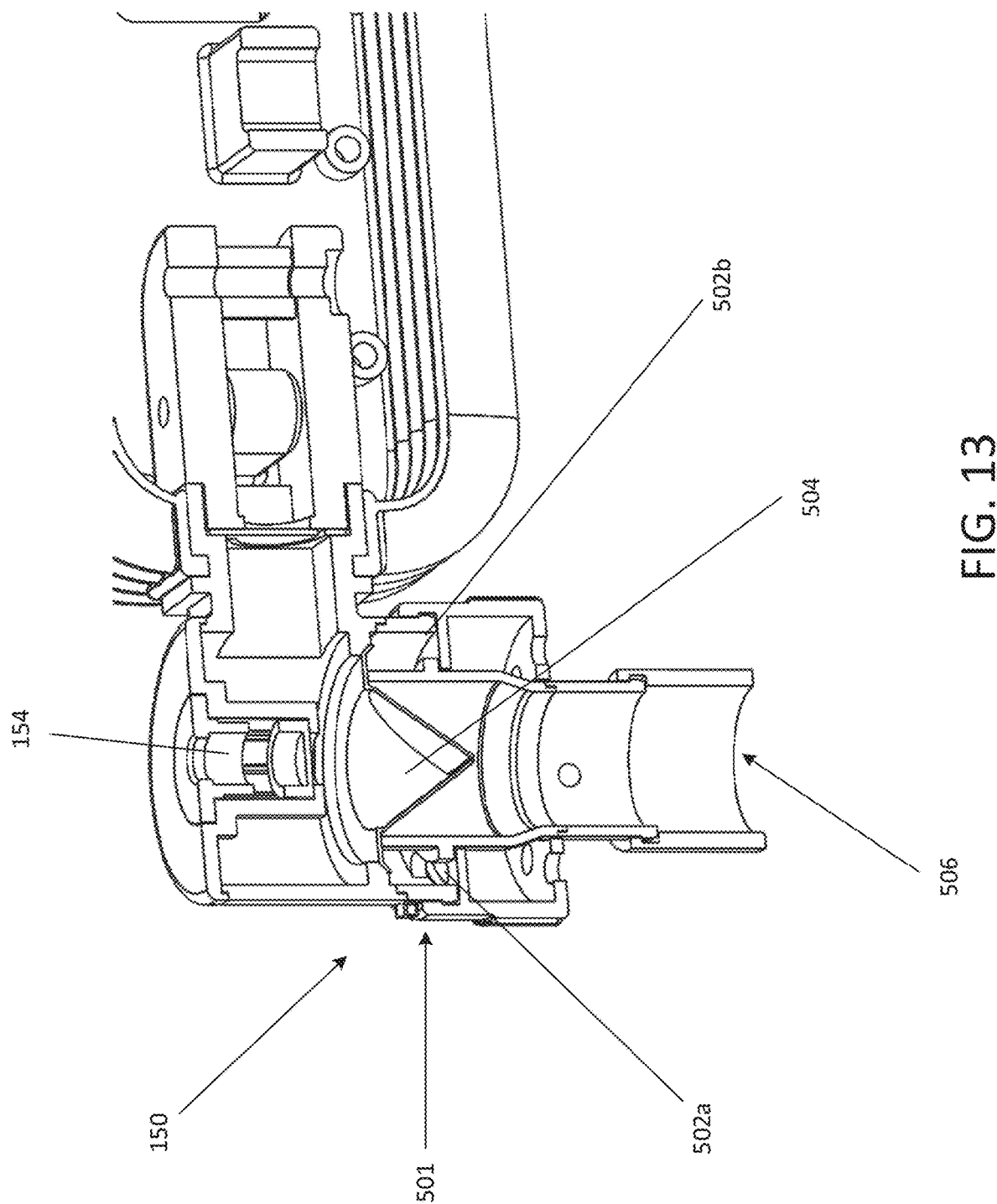
FIG. 13 illustrates a cross-sectional view of the two-way valve portion.

FIGS. 13-16 illustrate a cross-sectional view of the connection member 150. In particular, FIG. 13 shows the connection member 150 that includes the two-way valve 504 located centrally in the mask connection lumen 506. The two-way valve 504 includes two flaps that meet each other in a center of the mask connection lumen 506. The connection member 150 also includes the PEEP valve 501, which includes at least one barrel valve 502 located laterally to the two-way valve 504. For example, a first barrel valve 502a is located on a first side of the two-way valve 504, and a second barrel valve 502b is located on an opposing side of the duckbilled valve.

The PEEP valve 501 is controlled by a dial (not shown) and can be adjusted to a predetermined expiratory pressure amount. The PEEP valve 501 maintains the predetermined pressure in the lungs of the patient. The two-way valve 504 allow air from the expandable bag portion 102 to be provided to the patient, but does not allow exhaled air from the patient to escape. The two-way valve 504 forces exhaled air to be expelled through the PEEP valve 501.

Figure 14:
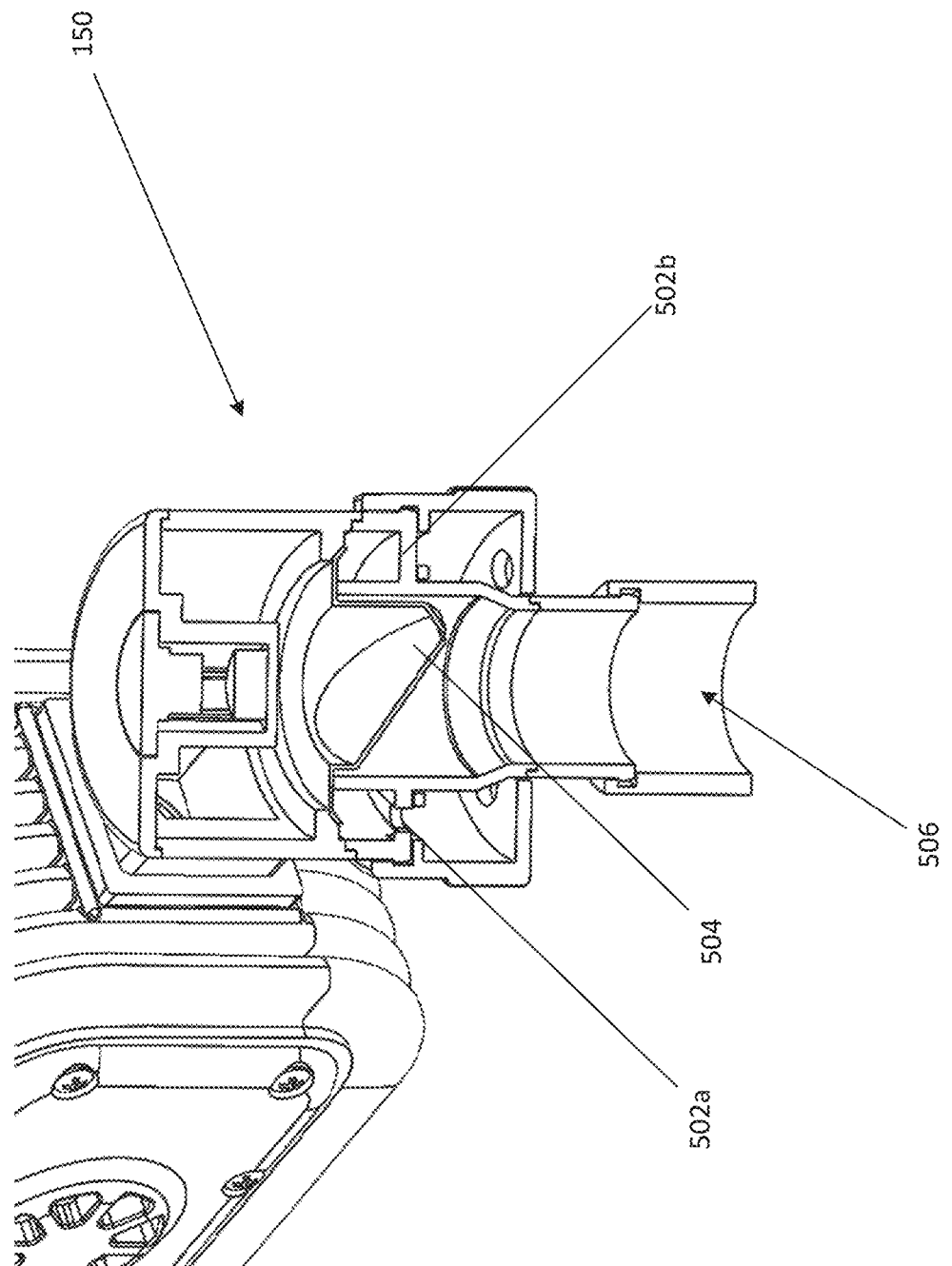
FIG. 14 illustrates a cross-sectional view of another embodiment of the two-way valve portion.
Figure 15:
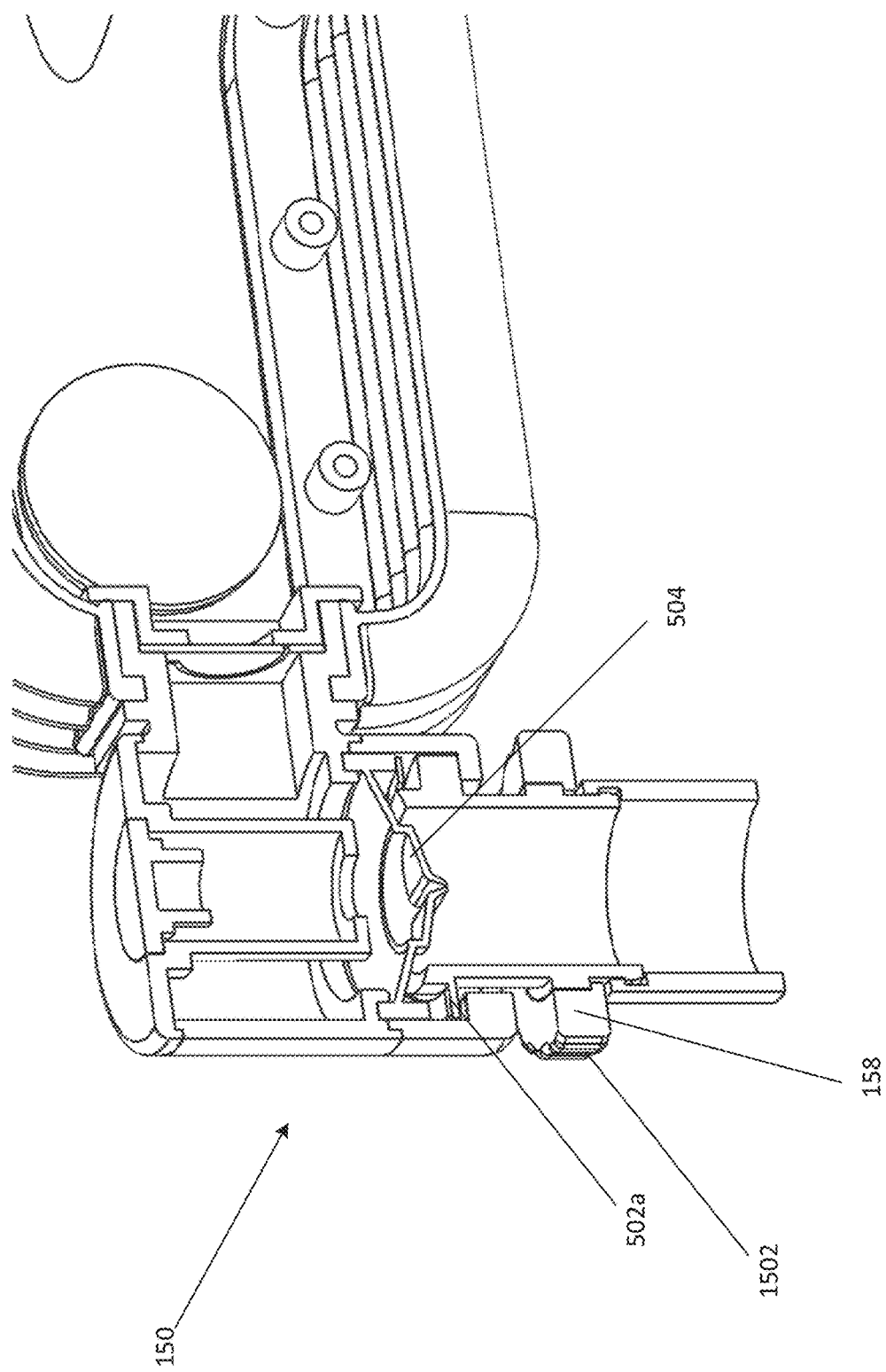
FIG. 15 illustrates a cross-sectional view of another embodiment of the two-way valve portion.
Figure 16:
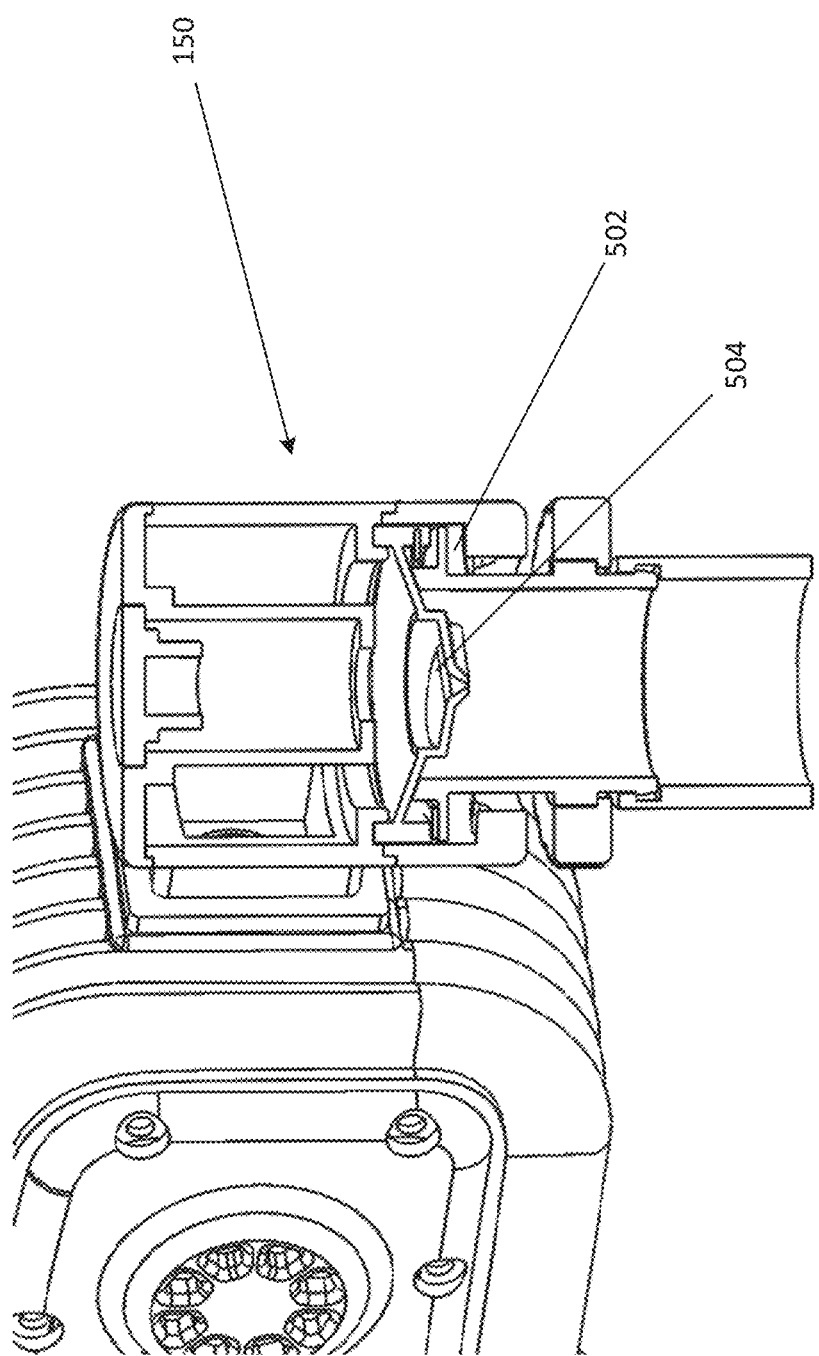
FIG. 16 illustrates a cross-sectional view of another embodiment of the two-way valve portion.

FIG. 14 illustrates an alternative embodiment of a two-way valve 504. For example the duckbilled valve includes only a single flap, where the single flap meets a side edge of the valve. FIGS. 15-16 also illustrate an alternative embodiment of a two-way valve 504 and a groove mechanism 1502 of a dial 158. The two-way valve 504 includes two flaps that meet in a middle portion, wherein the flaps have a small articulation before joining together.

Figure 17:
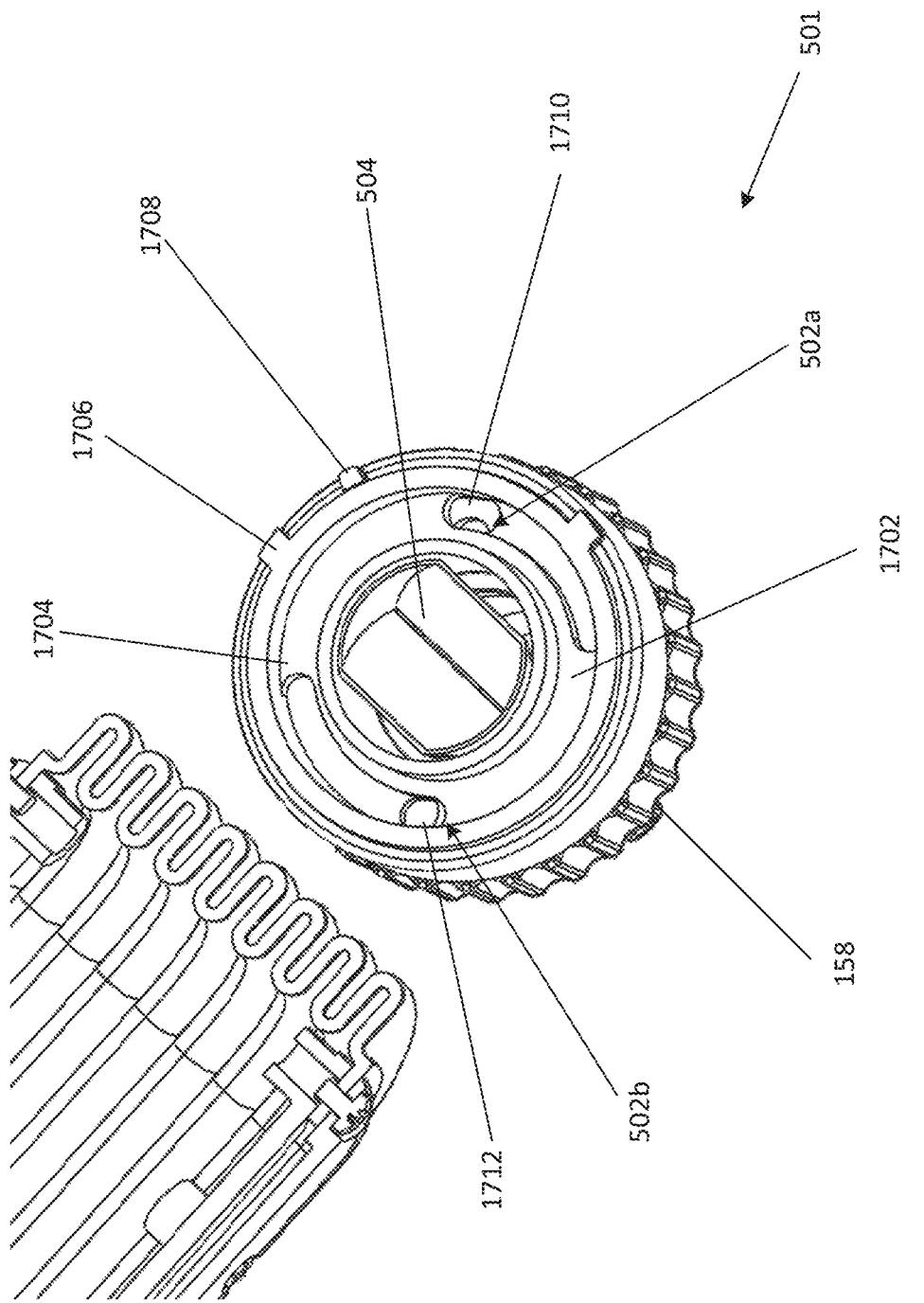
FIG. 17 illustrates a top cross-section view of the barrel-valve embodiment of the integrated PEEP valve.

FIG. 17 illustrates a top down cutaway view of the two-way valve 504 and the barrel valves 502a, 502b. The dial 158 controls the size of the barrel valves 502a, 502b. A user can rotate the dial 158 in a first direction to increase the size of the barrel valves 502, and can rotate the dial 158 in an opposing direction to decrease the size of the barrel valves 502.

The dial 158 is used to adjust the relative positions of cutouts 1702, 1704. When the dial 158 is turned fully in one direction, for example when fully turned clockwise, the cutouts 1702, 1704 do not overlap, which restricts the flow of exhaled air from the patient into the periphery. When the dial 158 is turned fully in the other direction, for example fully counterclockwise, the cutouts 1702, 1704 overlap, allowing exhaled air to readily vent into the periphery through the holes 1710, 1712 of the barrel valve 502b, 502b. The dial 158 can be set to an infinite number of positions between fully open, counterclockwise, and fully closed, clockwise allowing for infinite adjustments of PEEP.

Figure 18:
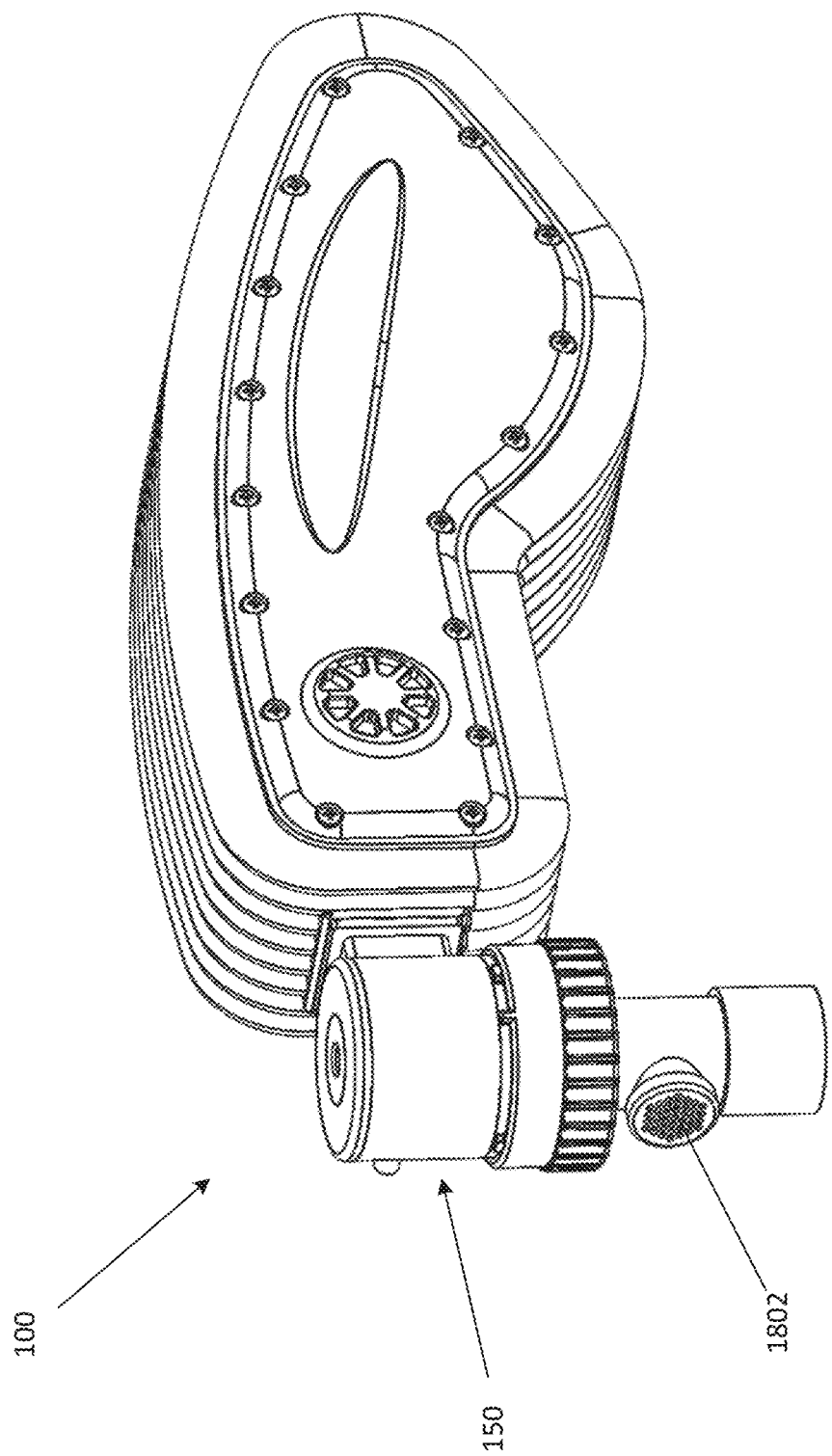
FIG. 18 illustrates a perspective view of an over breathing valve.

FIG. 18 illustrates an example expandable bag device 100 having an over breathing valve 1802 on the connection member 150. The over breathing valve 1802 is a one-way valve that allows a patient to inhale on their own, without the use of the air provided by the expandable bag portion 102. The over breathing valve 1802 may be a diaphragm valve, or any other type of one-way valve commonly known in the art. Exhalation from the patient, or positive pressure from the expandable bag portion 102, would effectively close this valve during operation.

Inside the over breathing valve 1802 may be an additional valve unit (not shown). The additional valve unit may be duck billed in shape or other potential embodiments. This valve allows the patient to inspire air from the periphery independent of whether or not the user is compressing the expandable bag portion 102 to deliver air to the patient. When the user compresses the expandable bag portion 102, the over breathing valve 1802 closes to prevent loss of inspiratory air from the bag to the periphery.

Figure 19:
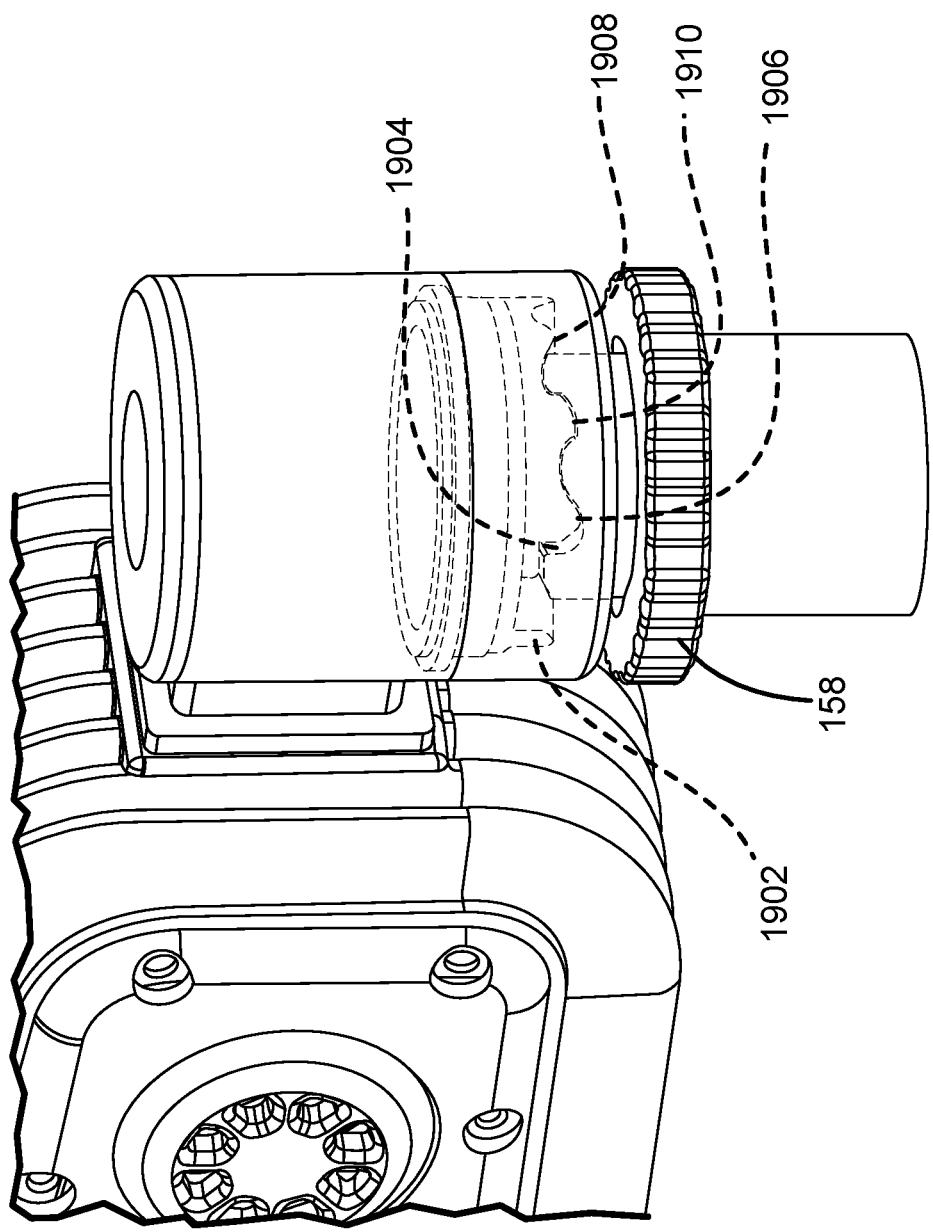
FIG. 19 illustrates an alternative view of a groove and track embodiment of an integrated PEEP valve.

FIG. 19 illustrates an alternative embodiment of a PEEP valve 501. The PEEP valve 501 includes a groove and track embodiment and a dial 158. The dial 158 is used to raise a lifting piece 1902 against a duckbilled-type valve. This is done by moving the relative position of lifting piece 1902 within the groove 1904. In this embodiment there are three potential positions of the lifting piece within the groove: a low position 1906, an intermediate position 1910, and a high position 1908. When the lifting piece 1902 is located in the low position 1906, the lifting piece 1902 is in its lower-most and least restrictive position against the duckbilled valve. This allows for ready exhalation from the patient and generates no PEEP. When the lifting piece 1902 is located in the intermediate potential position 1910, the lifting piece 1902 is lifted slightly against the duckbilled valve. This requires additional exhaled force in order to vent to the periphery and generates low PEEP. When the lifting piece 1902 is located in the high position 1908, the lifting piece 1902 is lifted tightly against the duckbilled valve. This requires substantial exhaled force in order to vent to the periphery and generates high PEEP. Additional positions within the groove 1904 could be added for additional adjustment of PEEP.

Figure 20:
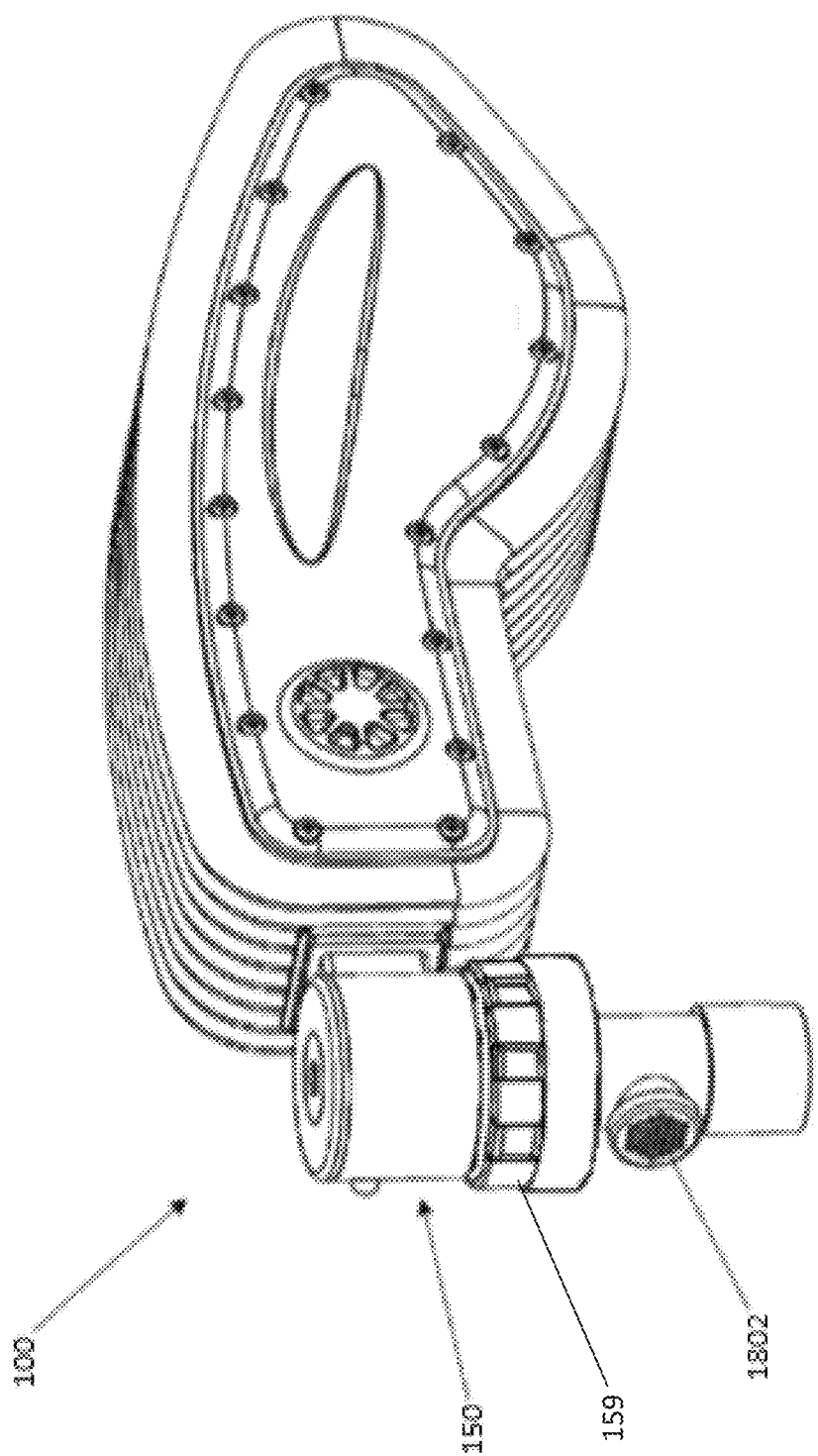
FIG. 20 illustrates an alternative embodiment of a PEEP controller.

FIG. 20 illustrates another embodiment of a PEEP controlling device. A push-button mechanism 159 is used to control the PEEP valve. The push-button mechanism 159 controls the positive end expiratory pressure (PEEP) valve, which is the controlled resistance of the exhaled airflow. The push-button mechanism 159 controls the location of side portions of an internal valve, such as a barrel valve (shown in FIGS. 13-17). When the push-button mechanism 159 is completed pushed to one end, the side portions move closer together, so it is harder for the patient to exhale against. When the push-button mechanism 159 is completed pushed to the alternative end, the side portions move farther apart, so it is easier for the patient to exhale against. The push-button mechanism 159 can have different values such as from 0 to 20 mmHg.

The push-button mechanism 159 may include a plurality of selectable buttons, each selectable button corresponds to a pre-determined value. A user is able to select the button that corresponds to the desired PEEP value.

In an alternative embodiment the PEEP controlling mechanism, in the form of a push-button mechanism 159 may generate PEEP by applying a plunger (not shown) that applied pressure against the upper aspect of the two-way valve 504. This plunger restricts lifting of the two-way valve 504 resisting exhalation and generating PEEP.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

The invention claimed is:

1. A respiratory device for providing respiratory support to a patient, the respiratory device comprising:
an expandable bag comprising an air intake valve, the expandable bag having an adjustable predetermined tidal volume and a hinge, the hinge configured to maintain the expandable bag in a predetermined capacity in an uncompressed configuration, and wherein after compression, the hinge is configured to reinflate the expandable bag at a predetermined rate;
a connection member in fluid communication with the expandable bag portion, the connection member comprising:
a duckbilled valve configured to allow air to move from the expandable bag portion in a first direction and directs air through a positive end-expiratory pressure (PEEP) valve in an opposing direction,
the PEEP valve comprising at least one adjustable aperture located adjacent the duckbilled valve, and a PEEP controller comprising a dial located around an external wall of the connection member, the dial configured to adjust the size of the at least one aperture; and
wherein the connection member is capable of connecting to a patient breathing interface.

2. The respiratory device of claim 1, wherein the expandable bag portion comprises a bellows and includes two rigid side portions that envelope the bellows.

3. The respiratory device of claim 1, wherein the positive end-expiratory pressure valve is a barrel valve.

4. The respiratory device of claim 1, wherein the dial has a plurality of settings to select a desired exhale pressure.

5. The respiratory device of claim 1, wherein the connection member further comprises a first external pressure gauge connection member and a second external pressure gauge connection member.

6. The respiratory device of claim 5, wherein the external pressure gauge connection members are configured to measure peak inspiratory pressure or positive end-expiratory pressure.

7. The respiratory device of claim 1, further comprising a pressure relief valve controller configured to select a pre-determined maximum peak inspiratory pressure.

8. The respiratory device of claim 1, further comprising a strap having a first end and a second end, the first end connectable to a first side of the expandable bag portion and the second end connectable to a second side of the expandable bag portion.

9. The respiratory device of claim 1, further comprising a tidal volume controller, the tidal volume controller configured to maintain a predetermined adjustable tidal volume of the expandable bag.

10. The respiratory device of claim 9, wherein the tidal volume controller comprises a dial.

11. The respiratory device of claim 1, further comprising a pressure relief valve configured to vent excess pressure from the connection member to an external environment.

12. A method of providing respiratory support to a patient, the method comprising:
providing a respiratory device comprising:
an expandable bag having a first end and a second end, the expandable bag comprising a hinge at the first end configured to reinflate the expandable bag at a predetermined rate and a rigid connection member connected to the first end and adjacent the hinge, and in fluid communication with the expandable bag, the rigid connection member having an inlet connected to the expandable bag, the inlet having a central axis, and an outlet configured to be connected to a patient breathing interface, the outlet having a central axis perpendicular to the central axis of the inlet, wherein the second end of the expandable bag expands a greater amount than the first end of the expandable bag when viewed along a plane defined by the central axis of the inlet and perpendicular to the central axis of the outlet; and
wherein the hinge is configured to open and close along an axis that is parallel to the central axis of the inlet; and
selecting a predetermined tidal volume of the expandable bag;
selecting a pressure of a positive end-expiratory pressure (PEEP) valve with a PEEP controller; and having a user compress the expandable bag to provide air to the patient, wherein the user is prevented from compressing the expandable bag beyond the predetermined tidal volume.

13. The method of claim 12, wherein the expandable bag is compressible by the user, and the expandable bag is inflatable via the hinge, the hinge configured to maintain the expandable bag to a predetermined adjustable capacity in an uncompressed configuration.

14. The method of claim 12, wherein the PEEP controller is a push-button comprising a plurality of selectable settings, each selectable setting corresponding to a predetermined value, and the method includes selecting one of the plurality of settings.

15. The method of claim 12, wherein selecting a predetermined tidal volume of the expandable bag includes connecting a first end of a strap to a first side of the expandable bag and connecting a second end of the strap to a second side of the expandable bag.

16. The method of claim 12, further comprising selecting a predetermined maximum peak inspiratory pressure.

17. The method of claim 12, wherein selecting the predetermined tidal volume controls a maximum tidal volume of the expandable bag.

18. A respiratory device for providing respiratory support to a patient, the respiratory device comprising:
an expandable bag having a first end and a second end, the expandable bag comprising:
an air intake valve; and
a hinge at the first end, the hinge configured to maintain the expandable bag in a predetermined capacity in an uncompressed configuration, and wherein after compression, the hinge is configured to reinflate the expandable bag; and
a rigid connection member connected to the first end of the expandable bag, adjacent the hinge, and in fluid communication with the expandable bag, the rigid connection member having an inlet connected to the expandable bag, the inlet having a central axis, and an outlet configured to be connected to a patient breathing interface, the outlet having a central axis perpendicular to the central axis of the inlet;
wherein the second end of the expandable bag expands a greater amount than the first end of the expandable bag when viewed along a plane defined by the central axis of the inlet and perpendicular to the central axis of the outlet; and
wherein the hinge is configured to open and close along an axis that is parallel along the central axis of the inlet of the connection member.

19. The respiratory device of claim 18, further comprising a pressure relief valve controller configured to select a predetermined maximum peak inspiratory pressure.

20. The respiratory device of claim 18, wherein the expandable bag comprises an adjustable predetermined tidal volume.

21. The respiratory device of claim 18, wherein the hinge is configured to reinflate the expandable bag at a predetermined rate.

22. A respiratory device for providing respiratory support to a patient, the respiratory device comprising:
an expandable bag comprising an air intake valve and a hinge, the hinge configured to maintain the expandable bag in a predetermined capacity in an uncompressed configuration, and wherein after compression the hinge is configured to reinflate the expandable bag;
a connection member in fluid communication with the expandable bag portion, the connection member comprising:
a duckbilled valve configured to allow air to move from the expandable bag portion in a first direction and directs air through a positive end-expiratory pressure (PEEP) valve in an opposing direction;
a PEEP controller comprising a dial and a lifting piece, wherein the PEEP controller is configured so that when the dial is turned, the dial lifts the lifting piece relative to the duckbilled valve to adjust a distance between the lifting piece and the duckbilled valve; and
wherein the connection member is capable of connecting to a patient breathing interface.

23. The respiratory device of claim 22, wherein the expandable bag comprises an adjustable predetermined tidal volume.

24. The respiratory device of claim 22, wherein the hinge is configured to reinflate the expandable bag at a predetermined rate.

* * * * *